United States Patent
King-Underwood et al.

(10) Patent No.: US 10,144,721 B2
(45) Date of Patent: *Dec. 4, 2018

(54) P38 MAP KINASE INHIBITORS

(71) Applicant: Respivert Ltd., Buckinghamshire (GB)

(72) Inventors: John King-Underwood, Pendock (GB); Ito Kazuhiro, Wallington (GB); Peter Strong, London (GB); William Garth Rapeport, London (GB); Catherine Elisabeth Charron, London (GB); Peter John Murray, Cheltenham (GB); Jonathan Gareth Williams, Nottingham (GB); Stuart Thomas Onions, Nottingham (GB)

(73) Assignee: Respivert Ltd., Buckinghamshire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/988,824

(22) Filed: Jan. 6, 2016

(65) Prior Publication Data

US 2016/0115152 A1  Apr. 28, 2016

Related U.S. Application Data

(63) Continuation of application No. 13/639,887, filed as application No. PCT/GB2011/050697 on Apr. 8, 2011, now Pat. No. 9,260,410.

(30) Foreign Application Priority Data

Apr. 8, 2010 (EP) .................................. 10159377

(51) Int. Cl.
  C07D 401/12  (2006.01)
  A61K 31/4439 (2006.01)
(52) U.S. Cl.
  CPC .................. C07D 401/12 (2013.01)
(58) Field of Classification Search
  None
  See application file for complete search history.

(56) References Cited

U.S. PATENT DOCUMENTS

| | | |
|---|---|---|
| 6,319,921 B1 | 11/2001 | Crillio et al. |
| 7,767,696 B2 | 8/2010 | Hoelzemann et al. |

FOREIGN PATENT DOCUMENTS

| | | |
|---|---|---|
| WO | WO 99/32106 A1 | 7/1999 |
| WO | WO 99/32110 A1 | 7/1999 |
| WO | WO 99/32455 A1 | 7/1999 |
| WO | WO 2000/43384 A1 | 7/2000 |
| WO | WO 03/00599 A2 | 1/2003 |
| WO | WO 2006/072589 A2 | 7/2006 |
| WO | WO 2007/087448 A1 | 8/2007 |
| WO | WO 2007/089512 A1 | 8/2007 |
| WO | WO 2010/038085 A2 | 4/2010 |
| WO | WO 2010/038086 A2 | 4/2010 |
| WO | WO 2010/067130 A1 | 6/2010 |
| WO | WO 2010/067131 A1 | 6/2010 |
| WO | WO 2010/112936 A1 | 10/2010 |
| WO | WO 11/070369 A1 | 6/2011 |
| WO | WO 2011/121366 A1 | 10/2011 |
| WO | WO 2011/124930 A1 | 10/2011 |

OTHER PUBLICATIONS

Williams et al (Foye's Principles of Medicinal Chemistry, 5th Edition, pp. 59-63, 2002).*
Patani et al (Chem Rev 96:3147-3176, 1996).*
Dumas et al., "Synthesis and pharmacological characterization of a potent, orally active p38 kinase inhibitor", Bioorganic & Medicinal Chemistry Letters (2002) 1559-1562 vol. 12, Pergamon.
Dumas et al., "1-Phenyl-5-pyrazolyl ureas: potent and selective p38 kinase inhibitors", Bioorganic & Medicinal Chemistry Letters (2000) 2051-2054 vol. 10 (18), Pergamon.
Regan et al., "Structure-activity relationships of the p38 alpha MAP kinase inhibitor 1-(5-tert-Butyl-2p-tolyl-2H-pyrazol-3y1)-3-[4-(2-morpholin-4-yl-ethoxy)naphthalene-1-yl]urea(BIRB 796)", J. Med. Chem (2003) 4676-4686 vol. 46 (22), American Chemical Society.
Dominguez et al., "p38 MAP kinase inhibitors: Many are made but few are chosen", Current Opinion in Drug Discovery and Development (2005) 421-430 vol. 8 (4), The Thomson Corporation.
Smith, S. et al., "Inhibitory effect of p38 mitogen-activated protein kinase inhibitors on cytokine release from human macrophages", J. Br. J. Pharmacol., 2006, 149:393-404.
Kuma, Y. "BIRB796 inhibits all p38 MAPK isoforms in vitro and in vivo", J. Biol. Chem., 2005, 280:19472-19479.
Hale, K. K. et al., "Differential Expression and Activation of p38 Mitogen-Activated Protein Kinase α, β, γ and δ in Inflammatory Cell Lineages", J. Immunol., 1999, 162(7):4246-52.
Underwood D.C. et al., "SB239063, a p38 MAPK inhibitor, reduces neutrophilia, inflammatory cytokines, MMP-9, and fibrosis in lung", Am. J. Physiol. Lung Cell. Mol. Physiol., 2000, 279:895-902.
Nath, P. et al., "Importance of p38 mitogen-activated protein kinase pathway in allergic airway remodeling and bronchial hyperresponsiveness", Eur. J. Pharmacol., 2006, 544:160-167.
Irusen, E. et al., "p38 Mitogen-activated protein kinase-induced glucocorticoid receptor phosphorylation reduces its activity: Role in steroid-insensitive asthma", J. Allergy Clin. Immunol., 2002, 109:649-657.

(Continued)

Primary Examiner — Marcos L Sznaidman
Assistant Examiner — Rayna Rodriguez
(74) Attorney, Agent, or Firm — McDermott Will & Emery LLP

(57) ABSTRACT

There is provided inter alia a compound of formula (I):

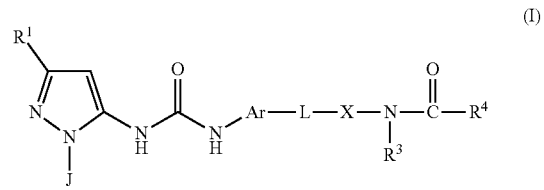

wherein $R^1$, J, Ar, L, X, $R^3$ and $R^4$ are as defined in the specification, for use in the treatment of inflammatory disorders.

13 Claims, No Drawings

(56) References Cited

OTHER PUBLICATIONS

Lee et al., "MAP Kinase p38 Inhibitors: Clinical Results and an Intimate Look at Their Interactions with p38α Protein", *Current Med. Chem.*, 2005, 12:2979-2994.

Mercado et al., "Formoterol restores costicosteroid sensitivity in severe asthma via p38 MAPK γ inhibition", American Thoracic Society Abstract, 2007.

Regan, et al., "The Kinetics of Bnding to p38MP Kinase by Analogues of BIRB 796", Bioorganic & Medicinal Chemistry Letters, 13:3101-3104, 2003.

Laufer et al., "Tetrasubstituted Imidazole Inhibitors of Cytokine Release: Probing Substituents in the N-1 Position", J. Medical Chemistry, 47:6311-6325, 2004.

\* cited by examiner

P38 MAP KINASE INHIBITORS

CROSS-REFERENCE TO RELATED APPLICATIONS

This application is a continuation application of U.S. application Ser. No. 13/639,887 filed Oct. 8, 2012, now allowed, which is a 371 of International Application Number PCT/GB 2011/050697, filed Apr. 8, 2011, which claims the benefit of European Application Number 10159377.0, filed Apr. 8, 2010. The entire contents of each of the aforesaid applications are incorporated herein by reference in their entirety.

FIELD OF THE INVENTION

The invention relates to compounds which are inhibitors of p38 mitogen-activated protein kinase enzymes (referred to herein as p38 MAP kinase inhibitors), for example the alpha and gamma kinase sub-types thereof, and their use in therapy, including in pharmaceutical combinations, especially in the treatment of inflammatory diseases, including inflammatory diseases of the lung, such as COPD.

BACKGROUND OF THE INVENTION

Four p38 MAPK isoforms (alpha, beta, gamma and delta respectively) have been identified, each displaying a tissue-specific expression pattern. The p38 MAPK alpha and beta isoforms are ubiquitously expressed throughout the body and are found in many different cell types. The p38 MAPK alpha and beta isoforms are inhibited by certain known small molecule p38 MAPK inhibitors. Earlier generations of compounds were highly toxic due to the ubiquitous expression pattern of these isoforms and off-target effects of the compounds. More recent inhibitors are improved to be highly selective for p38 MAPK alpha and beta isoforms and have a wider safety margin.

Less is known about the p38 MAPK gamma and delta isoforms. These isoforms are expressed in specific tissues/cells (unlike the p38 alpha and p38 beta isoforms). The p38 MAPK-delta isoform is expressed more in the pancreas, testes, lung, small intestine and kidney. It is also abundant in macrophages (Smith, S. J. (2006) *Br. J. Pharmacol*, 149: 393-404) and detectable in neutrophils, CD4+ T cells and endothelial cells (www.genecard.org. Karin, K. (1999) *J. Immunol*.). Very little is known about the expression of p38 MAPK gamma but it is expressed more in brain, skeletal muscle and heart, as well as in lymphocytes and macrophages (www.genecard.org).

Selective small molecule inhibitors of p38 MAPK-gamma and p38 MAPK-delta are not currently available, but one existing compound, BIRB 796, is known to have pan-isoform inhibitory activity. The p38 gamma and p38 delta inhibition is observed at higher concentrations of the compound than those required to inhibit p38 alpha and p38 beta (Kuma, Y. (2005) *J. Biol. Chem*. 280:19472-19479). BIRB 796 also impaired the phosphorylation of p38 MAPKs or JNKs by the upstream kinase MKK6 or MKK4. Kuma discussed the possibility that the conformational change caused by the binding of the inhibitor to the MAPK protein may affect the structure of both its phosphorylation site and the docking site for the upstream activator, therefore impairing the phosphorylation of p38 MAPKs or JNKs.

p38 MAP kinase is believed to play a pivotal role in many of the signalling pathways that are involved in initiating and maintaining chronic, persistent inflammation in human disease, for example, in severe asthma and COPD. There is now an abundant literature which demonstrates that p38 MAP kinase is activated by a range of pro-inflammatory cytokines and that its activation results in the recruitment and release of further pro-inflammatory cytokines. Indeed, data from some clinical studies demonstrate beneficial changes in disease activity in patients during treatment with p38 MAP kinase inhibitors. For instance Smith, S. J. (2006) *Br. J, Pharmacol*. 149:393-404 describes the inhibitory effect of p38 MAP kinase inhibitors on TNFα (but not IL-8) release from human PBMCs. Use of inhibitors of p38 MAP kinase in the treatment of chronic obstructive pulmonary disease (COPD) is proposed. Small molecule inhibitors targeted to p38 MAPKα/β have proved to be effective in reducing various parameters of inflammation in cells and tissues obtained from patients with COPD, who are generally corticosteroid insensitive, (Smith, S. J. (2006) *Br. J. Pharmacol*. 149:393-404) and in vivo animal models (Underwood, D. C. et al. *Am. J. Physiol*. (2000) 279:L895-902; Nath, P. et al., (2006) *Eur. J. Pharmacol*. 544; 160-167). Irusen and colleagues also suggested the possibility of involvement of p38 MAPKα/β on corticosteroid insensitivity via reduction of binding affinity of glucocorticoid receptor (GR) in nuclei (Irusen. E. et al., (2002) *J. Allergy Clin. Immunol*., 109:649-657). Clinical experience with a range of p38 MAP kinase inhibitors, including AMG548, BIRB 796, VX702, SCIO469 and SCIO323 is described in Lee et al. (2005) *Current Med. Chem*. 12:2979-2994.

COPD is a condition in which the underlying inflammation is reported to be substantially resistant to the anti-inflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. The recent publication of Mercado et al (2007; *American Thoracic Society Abstract A56*) demonstrates that silencing p38 gamma has the potential to restore sensitivity to corticosteroids. Thus there may be a "two pronged" benefit to the use of a p38 MAP kinase inhibitor for the treatment of COPD and severe asthma.

However, the major obstacle hindering the utility of p38 MAP kinase inhibitors in the treatment of human chronic inflammatory diseases has been the toxicity observed in patients. This has been sufficiently severe to result in the withdrawal from clinical development of many of the compounds progressed, including all those specially mentioned above.

There remains a need to identify and develop new compounds therapeutically useful as p38 MAP kinase inhibitors which have improved therapeutic potential, in particular which are more efficacious, longer acting and/or less toxic at the relevant therapeutic dose. An objective of the present invention is to provide compounds which inhibit p38 MAP kinase, for example with certain sub-type specificity, which show good anti-inflammatory potential, in particular suitable for use in therapy.

SUMMARY OF THE INVENTION

According to the invention there is provided a compound of formula (I)

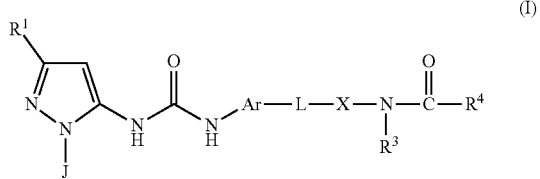

wherein;

J represents

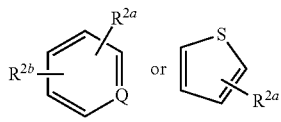

Ar is a naphthylene or phenyl ring either of which may be optionally substituted by one more groups (e.g. 1, 2 or 3 groups) independently selected from $C_{1-6}$ alkyl, $C_{1-6}$ alkoxy, amino. $C_{1-4}$ mono alkyl amino and $C_{2-8}$ di-alkyl amino;

Q is N, or CH;

$R^1$ is H, phenyl, or a saturated or unsaturated branched or unbranched $C_{1-10}$ alkylene in the form of an acyclic or alicyclic chain wherein one or more carbons in the chain (for example 1 to 3, such as 1, 2 or 3 carbons) are optionally replaced by a heteroatom(s) independently selected from —O—, —N— and $S(O)_n$ and the chain is optionally substituted by:

one oxo group, and/or one or more halogen atoms (for example 1 to 6);

$R^{2a}$ is H, halo, saturated or unsaturated branched or unbranched $C_{1-6}$ alkylene chain, wherein one or more carbons (for example 1 to 3, such as 1, 2 or 3 carbons) are optionally replaced by a heteroatom(s) independently selected from —O—, —N— and/or $S(O)_m$ and the chain is optionally substituted by one or more halogen atoms (for example 1 to 6);

$R^{2b}$ is H, halo, $C_{1-6}$ alkoxy or $C_{1-6}$ alkyl optionally substituted by OH:

L is saturated or unsaturated branched or unbranched $C_{1-6}$ alkylene chain (such as a $C_{1-3}$ alkylene), wherein one or more carbons (for example 1 to 3, such as 1, 2 or 3 carbons) are optionally replaced by a heteroatom selected from —O— and/or S. and the chain is optionally substituted by one or two oxo groups (for example 1 or 2);

X is a pyridine or pyrimidine ring optionally substituted by $C_{1-3}$ alkyl, or $C_{1-3}$ haloalkyl;

$R^3$ H or $C_{1-4}$ alkyl;

$R^4$ is $C_{1-10}$ branched or unbranched acyclic or alicyclic alkyl chain n is 0, or 2;

m is 0, 1 or 2;

or a pharmaceutically acceptable salt thereof, including all stereoisomers, tautomers and isotopic derivatives thereof.

DETAILED DESCRIPTION OF THE INVENTION

The compounds of the invention are kinase inhibitors, possessing, for example, potent inhibitory activity at p38 MAPK enzymes and may show selectivity for the p38-alpha isoform over the p38-gamma isoform. The compounds display efficacy in established in vitro assays of anti-inflammatory activity. For example compounds of the invention demonstrate the ability to block LPS-induced TNFα release from differentiated U937 cells and THP-1 cells and similarly to block the stimulated release of IL-8 from differentiated U937 cells.

According to the invention the compounds provided herein are especially suitable for treating inflammatory pulmonary diseases by topical administration since they are believed to have properties that result in long residency times in the lung, resulting in an extended duration of therapeutic action, which is consistent with twice or even once, daily dosing.

In addition it is believed that one or more compounds of the invention may also possess certain antiviral activities making them useful for preventing or ameliorating the symptoms of viral infection in patients, for example with inflammatory lung disorders.

The properties, described above (alone or in combination), distinguish the compounds according to the invention from other known compounds, which do not possess these desirable so features.

Alkyl as used herein refers to straight chain or branched chain alkyl, such as, without limitation, methyl, ethyl, n-propyl, iso-propyl, butyl, n-butyl and tert-butyl. In one embodiment alkyl refers to straight chain alkyl.

Alkoxy as used herein refers to straight or branched chain alkoxy, for example methoxy, ethoxy, propoxy, butoxy. Alkoxy as employed herein also extends to embodiments in which the oxygen atom is located within the alkyl chain, for example —$C_{1-3}$ alkyl$OC_{1-3}$ alkyl, such as —$CH_2CH_2OCH_3$ or —$CH_2OCH_3$. Thus in one embodiment the alkoxy is linked through carbon to the remainder of the molecule. In one embodiment the alkoxy is linked through oxygen to the remainder of the molecule, for example —$OC_{1-6}$ alkyl. In one embodiment the disclosure relates to a straight chain alkoxy.

Heteroalkyl as employed herein is intended to refer to a branched or straight chain alkyl wherein one or more, such as 1, 2 or 3 carbons are replaced by a heteroatom, selected from N, O or $S(O)_r$, wherein r represents 0, 1 or 2. The heteroatom may replace a primary, secondary or tertiary carbon, that is, for example, SH, OH or $NH_2$ for $CH_3$, or NH or O or $SO_2$ for —$CH_2$— or N for a —CH— or a branched tertiary carbon, as technically appropriate.

Haloalkyl as employed herein refers to alkyl groups having 1 to 6 halogen atoms, for example 1 to 5 halogens, including perhaloalkyl, in particular perchloroalkyl or perfluoroalkyl, more specifically —$CCl_3$, —$CF_2CF_3$ or $CF_3$.

$C_{1-4}$ mono acyl amino and $C_{2-8}$ di-acyl amino are intended to refer to —NHC(O)$C_{1-4}$ alkyl and to —N(C=O$C_{1-4}$alkyl)(C=O$C_{1-4}$ alkyl) respectively.

$C_{1-4}$ mono alkyl amino and $C_{2-8}$ di-alkyl amino are intended to refer to —NH$C_{1-4}$ alkyl and to —N($C_{1-4}$ alkyl)($C_{1-4}$ alkyl) respectively.

Aryl as used herein refers to, for example $C_{6-14}$ mono or polycyclic systems having from 1 to 3 rings wherein at least one ring is aromatic including phenyl, naphthyl, anthracenyl, 1,2,3,4-tetrahydronaphthyl and the like, such as phenyl and naphthyl.

Heteroaryl is a 6 to 10 membered aromatic monocylic ring or bicyclic ring system wherein at least one ring is an aromatic nucleus comprising one or more, for example 1, 2, 3 or 4 heteroatoms independently selected from O, N and S. Examples of heteroaryls include: pyrrole, oxazole, thiazole, isothiazole, imidazole, pyrazole, isoxazole, pyridine, pyridazine, pyrimidine, pyrazine, benzothiophene, benzofuran, or 1, 2, 3 and 1, 2, 4 triazole.

Heterocyclyl as employed herein refers to a 5 to 6 membered saturated or partially unsaturated non-aromatic ring comprising one or more, for example 1, 2, 3 or 4 heteroatoms independently selected from O, N and S optionally one or two carbons in the ring may bear an oxo substituent. The definition of $C_{5-6}$ heterocycle as employed herein refers to a 5 to 6 membered saturated or partially unsaturated non-aromatic carbocyclic ring comprising one or more, for example 1, 2, 3 or 4 heteroatoms independently selected from O, N and S, wherein each heteroatom replaces a carbon atom and optionally one or two carbons may bear an oxo substitutent. Clearly any valancies of a heteroatom not employed in forming or retaining the ring structure may be filled by hydrogen or a substituent, as appropriate. Thus substituents on heterocycles may be on carbon or on a heteroatom, such as nitrogen as appropriate. Examples of heterocycles and $C_{5-6}$ heterocycles include pyrroline, pyrrolidine, tetrahydrofuran, tetrahydrothiophene, pyrazoline, imidazoline, pyrazolidine, imidazolidine, oxoimidazolidine, dioxolane, thiazolidine, isoxazolidine, pyran, dihydropyran, piperidine, piperazine, morpholine, dioxane, thiomorpholine and oxathiane.

Halogen includes fluoro, chloro, bromo or iodo, in particular fluoro, chloro or bromo, especially fluoro or chloro.

Oxo as used herein refers to C=O and will usually be represented as C(O).

$C_{3-8}$ cycloalkyl as employed herein is intended to refer to a saturated or partially unsaturated non-aromatic ring containing 3 to 8 carbon atoms, where the ring contains less than 8 carbons the ring may optionally bear one or more alkyl groups such that the number of carbon atoms in the ring plus the number of carbons in the alkyl substituents is not more than eight in total or 10 in the case of $C_{3-10}$ cycloalkyls.

$C_{1-10}$ alkyl includes $C_2$, $C_3$, $C_4$, $C_5$, $C_6$, $C_7$, $C_8$ or $C_9$ as well as $C_1$ and $C_{10}$.

$C_{0-8}$ alkyl includes $C_1$, $C_2$, $C_3$, $C_4$, $C_5$, $C_6$, or $C_7$ as well as $C_0$ and $C_8$.

In relation to a saturated or unsaturated, branched or unbranched $C_{1-10}$ alkyl chain (or similar language used herein), wherein at least one carbon (for example 1, 2 or 3 carbons, suitably 1 or 2, in particular 1) is replaced by a heteroatom selected from O, N, $S(O)_p$, wherein said chain is optionally, substituted by one or more groups independently selected from oxo and halogen, it will be clear to persons skilled in the art that the heteroatom may replace a primary, secondary or tertiary carbon, that is $CH_3$, —$CH_2$— or a —CH—, a tertiary carbon group or —CH=, as technically appropriate.

Saturated or unsaturated, branched or unbranched $C_{1-10}$ alkyl alicyclic chain is intended to refer to $C_{3-10}$ cycloalkyl.

In one embodiment J represents:

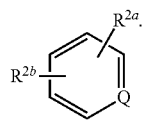

In one embodiment J represents:

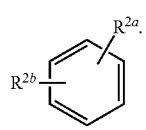

In one embodiment $R^1$ is —$C_{1-6}$ alkyl optionally substituted by OH, $C_{3-10}$ cycloalkyl, $C_{3-10}$ heterocycloalkyl, $C_{1-6}$ haloalkyl, $C_{1-6}$ alkylOC(O)$CH_3$.

In one embodiment of the disclosure there is provided compounds of formula (I), wherein $R^1$ is methyl, ethyl, propyl, iso-propyl, butyl or tert-butyl, in particular tert-butyl.

In one embodiment $R^1$ is —$C(CH_3)_2CH_2OH$.

In one embodiment $R^1$ is cyclopropyl, or 1-methylcyclopropyl, cyclopentyl, cyclohexyl, or 1-methylcyclohexyl, or adamantly.

In one embodiment $R^1$ is tetrahydropyranyl or 4-methyl-tetrahydro-2H-pyran-4-yl.

In one embodiment $R^1$ is —$CF_3$, —$CF_2CF_3$ or —$CCl_3$.

In one embodiment $R^1$ is phenyl.

In one embodiment the substituent $R^{2a}$ is in the 2, 3, or 4 position (i.e. ortho, meta or para position), in particular the para (4-) position relative to the attachment of the aromatic ring J to the pyrazole system.

In one embodiment $R^{2a}$ is methyl, ethyl, n-propyl, iso-propyl, n-butyl or tert-butyl, in particular methyl, for example in position 3 or 4.

In one embodiment $R^{2a}$ is —OH, for example in position 3 or 4.

In one embodiment $R^{2a}$ is halo such as chloro, for example in position 3 or 4.

In one embodiment $R^{2a}$ is —$C_{1-6}$ alkyl substituted by a hydroxyl group such as —$CH_2OH$, for example in position 3 or 4.

In one embodiment $R^{2a}$ is —$C_{1-6}$ alkoxy, such as —$OCH_3$, for example in position 3 or 4.

In one embodiment $R^{2a}$ is —$SC_{1-6}$ alkyl, such as —$SCH_3$, for example in position 3 or 4.

In one embodiment $R^{2a}$ is —$SO_2C_{1-6}$ alkyl, such as —$SO_2CH_3$ for example in the 3 or 4 position.

In one embodiment $R^{2a}$ is —$OCF_3$, for example located in position 3 or 4.

In one embodiment $R^{2a}$ is —NR'R" wherein R' is H, —$C_{1-3}$ alkyl or —$SO_2C_{1-3}$alkyl, and R" is H or —$C_{1-3}$ alkyl, for example located in position 3 or 4. In one embodiment $R^{2a}$ is —$NH_2$, for example in position 3 or 4.

In one embodiment $R^{2a}$ is —$NHSO_2CH_3$, for example in position 3 or 4.

In one embodiment $R^{2b}$ is H.

In one embodiment $R^{2b}$ is halo such as chloro, for example in position 3.

In one embodiment $R^{2a}$ is chloro and $R^{2b}$ is chloro, for example 3,4-dichloro.

In one embodiment $R^{2a}$ chloro is and $R^{2b}$ is —$OCH_3$, for example in positions 3,4 respectively.

In one embodiment $R^{2a}$ is —$OCH_3$ and $R^{2b}$ is —$OCH_3$, for example in position 3,4.

In one embodiment $R^{2a}$ chloro is and $R^{2b}$ is —OH, for example in position 3,4 respectively.

In one embodiment the substituent $R^{2a}$ is in the 2, 3, or 4 position (i.e. ortho, meta or para position), in particular the para (4-) position relative to the attachment of the aromatic ring J to the pyrazole system.

In one embodiment $R^{2a}$ is methyl, ethyl, n-propyl, iso-propyl, n-butyl or tert-butyl, in particular methyl, for example in position 3 or 4.

In one embodiment R$^{2a}$ is —OH, for example in position 3 or 4.

In one embodiment R$^{2a}$ is halo such as chloro, for example in position 3 or 4.

In one embodiment R$^{2a}$ is —C$_{1-6}$ alkyl substituted by a hydroxyl group such as —CH$_2$OH, for example in position 3 or 4.

In one embodiment R$^{2a}$ is —C$_{1-6}$ alkoxy, such as —OCH$_3$, for example in position 3 or 4.

In one embodiment R$^{2a}$ is —SC$_{1-6}$ alkyl, such as —SCH$_3$, for example in position 3 or 4.

In one embodiment R$^{2a}$ is —SO$_2$C$_{1-6}$ alkyl, such as —SO$_2$CH$_3$ for example in the 3 or 4 position.

In one embodiment R$^{2a}$ is —OCF$_3$, for example located in position 3 or 4.

In one embodiment R$^{2a}$ is —NR'R" wherein R' is H, —C$_{1-3}$ alkyl or —SO$_2$C$_{1-3}$alkyl, and R" is H or —C$_{1-3}$ alkyl, for example located in position 3 or 4. In one embodiment R$^{2a}$ is —NH$_2$, for example in position 3 or 4.

In one embodiment R$^{2a}$ is —NHSO$_2$CH$_3$, for example in position 3 or 4.

In one embodiment R$^{2b}$ is H.

In one embodiment R$^{2b}$ is halo such as chloro, for example in position 3.

In one embodiment R$^{2a}$ is chloro and R$^{2b}$ is chloro, for example 3,4-dichloro.

In one embodiment R$^{2a}$ chloro is and R$^{2b}$ is —OCH$_3$, for example in positions 3,4 respectively.

In one embodiment R$^{2a}$ is —OCH$_3$ and R$^{2b}$ is —OCH$_3$, for example in position 3,4.

In one embodiment R$^{2a}$ chloro is and R$^{2b}$ is —OH, for example in position 3,4 respectively.

In embodiments of the invention wherein the group Q represents N, the substituents R$^{2a}$ and R$^{2b}$ on the ring are pharmaceutically acceptable and do not include those of a highly reactive nature (such as a halogen atom disposed ortho to the heteroatom) such that compounds of formula (I) would thereby be rendered unstable and consequently unsuitable for their intended utility.

In one embodiment J is pyridine and R$^{2a}$ is methyl, ethyl, n-propyl, iso-propyl, n-butyl or tert-butyl, in particular methyl, for example in position 2 or 3.

In one embodiment J is pyridine and R$^{21}$ is —C$_{1-6}$ alkyl substituted by a hydroxyl group such as —CH$_2$OH, for example in position 2 or 3.

In one embodiment J is pyridine and R$^{2a}$ is —C$_{1-6}$ alkoxy, such as —OCH$_3$, for example in position 2 or 3.

In one embodiment J is pyridine and R$^{2a}$ is —SC$_{1-6}$ alkyl, such as —SCH$_3$, for example in position 2 or 3.

In one embodiment J is pyridine and R$^{2a}$ is —SO$_2$C$_{1-6}$ alkyl, such as —SO$_2$CH$_3$ for example in the 3 position.

In one embodiment J is pyridine and R$^{2a}$ is —OCF$_3$, for example located in position 3.

In one embodiment when J is pyridine and R$^{2a}$ is —NR'R" wherein R' is H, —C$_{1-3}$ alkyl or —SO$_2$C$_{1-3}$alkyl, and R" is H or —C$_{1-3}$ alkyl, for example located in position 2 or 3. In one embodiment R$^{2a}$ is —NH$_2$, for example in position 2 or 3.

In one embodiment J is pyridine and R$^{2a}$ is —NHSO$_2$CH$_3$, for example in position 2 or 3.

In one embodiment J is pyridine and R$^{2b}$ is H.

In one embodiment L represents O, CH$_2$, C=O or S(O)$_t$ where t is 0, 1 or 2, in particular 0 or 2.

In one embodiment L represents —OCH$_2$— or —OCH$_2$CH$_2$—.

In one embodiment X is pyridine.

In one embodiment R$^3$ is H.

In one embodiment R$^4$ is an unbranched alkyl, for example methyl, ethyl, propyl, butyl, pentyl, hexyl, nonyl, decyl, such as methyl.

In one embodiment R$^4$ is a branched alkyl, for example —CH$_2$CH(CH$_3$)$_2$, —C(CH$_3$)$_3$, CH$_2$CH(CH$_3$)CH$_2$CH$_3$ and the like.

In one embodiment the disclosure relates to compounds of formula (IA):

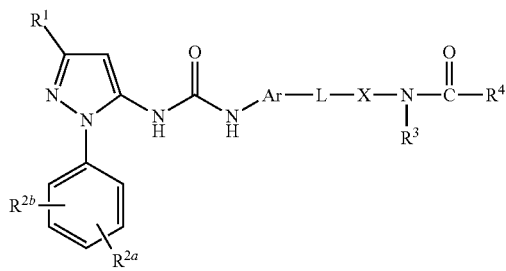

(IA)

wherein Ar, R$^1$, R$^{2a}$, R$^{2b}$, R$^3$, R$^4$, L and X, are as defined above for compounds of formula (I).

In one embodiment the disclosure relates to compounds of formula (IB):

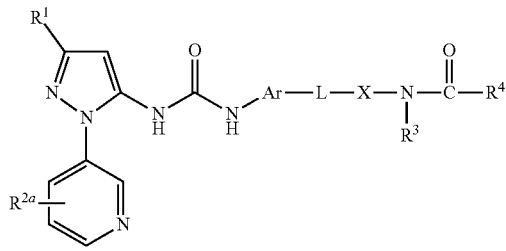

(IB)

wherein Ar, R$^1$, R$^{2a}$, R$^3$, R$^4$, L and X are as defined above for compounds of formula (I).

In one embodiment the disclosure relates to compounds of formula (IC):

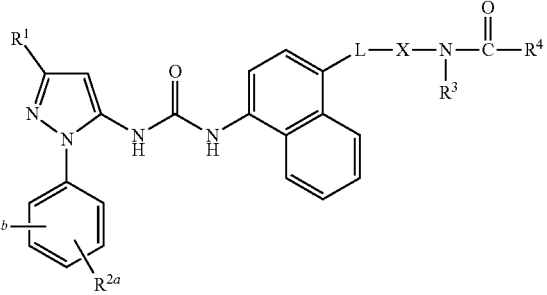

(IC)

wherein R$^1$, R$^{2a}$, R$^{2b}$, R$^3$, R$^4$, L and X are as defined above for compounds of formula (I).

In one embodiment the disclosure relates to compounds of formula (ID):

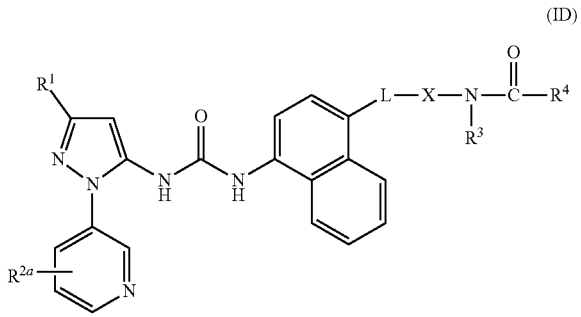

wherein $R^1$, $R^{2a}$, $R^3$, $R^4$, L and X are as defined above for compounds of formula (I).

In one embodiment the disclosure relates to compounds of formula (IE):

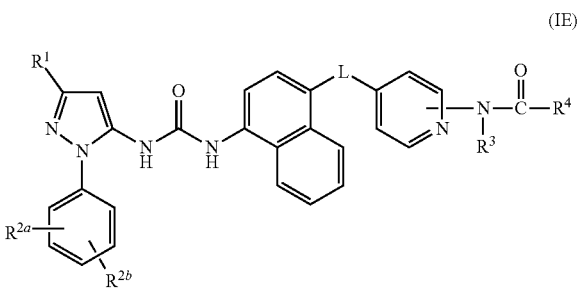

wherein $R^1$, $R^{2a}$, $R^{2b}$, $R^3$, $R^4$ and L are as defined above for compounds of formula (I).

In one embodiment of the invention the compounds of formula (IE) comprise of structures in which the substituent —$NR^3C(O)R^4$ is located at position 2 of the pyridine ring.

In one embodiment the disclosure relates to compounds of formula (IF):

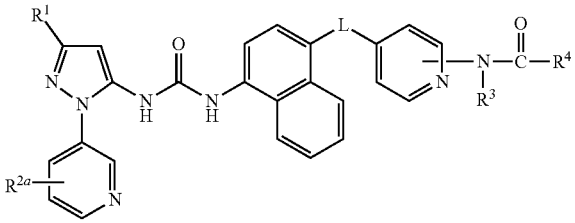

wherein $R^1$, $R^{2a}$, $R^3$, $R^4$ and L are as defined above for compounds of formula (I).

In one embodiment of the invention the compounds of formula (IF) comprise of structures in which the substituent —$NR^3C(O)R^4$ is located at position 2 of the pyridine ring.

In one embodiment the compound is:
N-(4-(2-(4-(3-(3-tert-Butyl)-1-p-tolyl-1H-pyrazol-5-yl) ureido)naphthalen-1-yloxy)ethyl)pyridin-2-yl)acetamide;
N-(4-(((4-(3-(3-(tert-Butyl)-1-(p-tolyl)-1H-pyrazol-5-yl) ureido)naphthalen-1-yl)oxy)methyl)pyridin-2-yl)acetamide;
N-(4-((4-(3-(3-(tert-Butyl)-1-(p-tolyl)-1H-pyrazol-5-yl) ureido)naphthalen-1-yl)oxy)pyridin-2-yl)acetamide;
or a pharmaceutically acceptable salt of any one thereof, including all stereoisomers, tautomers and isotopic derivatives thereof.

Examples of salts of compound (I) include all pharmaceutically acceptable salts, such as, without limitation, acid addition salts of mineral acids such as HCl and HBr salts and addition salts of organic acids such as a methanesulfonic acid salt. Further example salts include pharmaceutically acceptable acid addition salts which can conveniently be obtained by treating the base form with an appropriate acid, for example, inorganic acids such as sulfuric, nitric and phosphoric acids: or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, ethanesulfonic, benzenesulfonic, p-toluenesulfonic, cyclamic, salicylic, p-aminosalicylic or pamoic acids.

The disclosure herein extends to solvates of compounds of formula (I). Examples of solvates include hydrates.

The compounds of the disclosure include those where the atom specified is a naturally occurring or non-naturally occurring isotope. In one embodiment the isotope is a stable isotope. Thus the compounds of the disclosure include, for example, deuterium containing compounds and the like.

The compounds described herein may include one or more stereogenic centres, and the disclosure extends to include racemates, and to both enantiomers (for example each substantially free of the other enantiomer) and all stereoisomers, such as diastereomers resulting therefrom. In one embodiment one enantiomeric form is present in a purified form that is substantially free of the corresponding entaniomeric form.

The disclosure also extends to all polymorphic forms of the compounds herein defined.

Compounds of formula (I) can be prepared by a process comprising reacting a compound of formula (II):

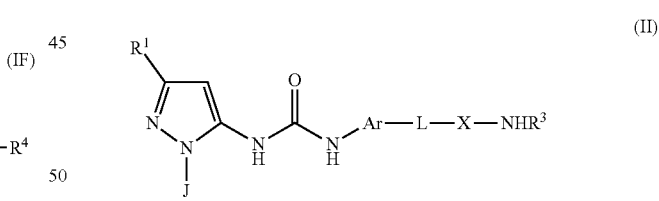

wherein J, L X, $R^1$, $R^3$ and Q are as defined above for compounds of formula (I) with a compound of formula (III):

Where $R^4$ is as defined above and $LG_1$ is a leaving group for example halogen, such as chloro. The reaction is suitably carried out in the presence of an organic base such as DIPEA or triethylamine and in an aprotic solvent or solvent mixture such as a mixture of DCM and DMF.

Alternatively compounds of formula (I) can be prepared by reacting a compound of formula (V):

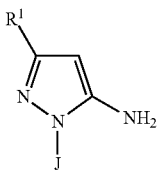
(V)

where $R^1$ and J are as defined above for compounds of formula (I), with a compound of formula (IV):

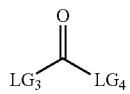
(IV)

wherein $LG_3$ and $LG_4$ each independently represent leaving groups, to generate a compound of formula (VIa), for example when $LG_3$ and $LG_4$ both represent imidazolyl; or a compound of formula (VIb), for example when the groups $LG_3$ and $LG_4$ represent halogen, such chloro or trihalomethoxy such as trichloromethoxy)

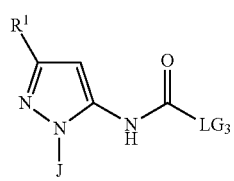
(VIa)

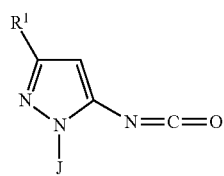
(VIb)

followed by reaction with a compound of formula (VII):

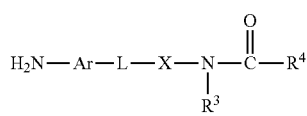
(VII)

wherein $R^3$, $R^4$, L, X, and Ar are as defined above for compounds of formula (I). The reaction is suitably carried out in an aprotic solvent such as dichloromethane in the presence of a sterically hindered base, for example DIPEA.

It will be understood by persons skilled in the art that compounds represented by formulae (VIa) and (VIb) are generally reactive intermediates, and may be formed in situ and reacted directly, without isolation, with a compound of formula (VII) to provide a compound of formula (I). Furthermore it will be understood by those skilled in the art that the use of appropriate protective groups may be required during the processes described above, for any of the groups $R^1$, $R^{2a}$ and $R^{2b}$ on J that comprise chemically sensitive functional groups, for example that contain a OH group or an $NH_2$ function Compounds of formula (II) can be prepared by reacting a compound of formula (VIII) wherein $R^3$, Ar, L and X are as defined above for compounds of formula (I)

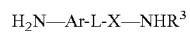
(VIII)

with a compound of formula (VIa) or a compound of formula (VIb), generated as described above from a compound of formula (V), in an aprotic solvent such as dichloromethane and a suitable base, for example DIPEA, employing, where necessary, appropriate protective groups for chemically sensitive functionality.

Compounds of formula (VII) may be prepared by reacting a compound of formula (IX):

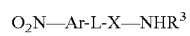
(IX)

wherein $R^3$, Ar, L and X are as defined above for compounds of formula (I), with a compound of formula (III). The reaction is suitably carried out in the presence of an organic base such as DIPEA or triethylamine in an aprotic solvent or solvent mixture, such as DCM and DMF.

From the intermediate so generated compounds of formula (VII) are then revealed by reduction of the nitro arene to the corresponding amine, for example by hydrogenation in the presence of a suitable catalyst, such as palladium on carbon. In certain cases it may be advantageous to conduct the reduction step chemically, for example under dissolving metal conditions, such as with iron in glacial acetic acid.

Compounds of formula (V) can be derived from the condensation of a phenylhydrazine of formula (X) or (Xa):

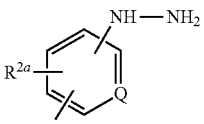
(X)

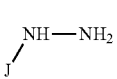
(Xa)

wherein J, $R^{2a}$, $R^{2b}$ and Q are as are defined above for compounds of formula (I), with a compound of formula (XI):

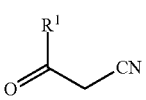
(XI)

wherein $R^1$ is as defined above for compounds of formula (I).

The reaction may be effected in an alcoholic solvent such as ethanol and in the presence of a mineral acid, such as HCl followed by treatment with a base, such as lithium hydroxide, in a solvent such as THF, to liberate the product as a free base.

Compounds of formula (I) wherein any of the substituents $R^1$ or $R^{2a}$ or $R^{2b}$ contains a sensitive functional group may be prepared from a compound of formula (V), by the processes described above, in which the said functionality is suitably protected during the synthetic transformations, followed by an appropriate deprotection step. For example a compound of formula (V) in which $R^1$, or $R^{2a}$ or $R^{2b}$ comprises a hydroxyalkyl, may be converted into a compound of formula (I) by the methods described above, by protecting the hydroxyl functionality, for example as a silyl ether. The hydroxyl group can be revealed at the end of the synthetic sequence by cleavage of the protective group: for example a silyl protective group may be removed with, for example, tetrabutylammonium fluoride.

Compounds of formula (V) wherein any of the substituents $R^1$, or $R^{2a}$ or $R^{2b}$ consists of a hydroxyalkyl such as, for example, $—(CH_2)_xCH_2OH$ may be prepared by the reduction of compounds of formula (V) in which one or more of the substituents $R^1$, or $R^{2a}$ or $R^{2b}$ comprises of the corresponding acid such as, for example $—(CH_2)_xCO_2H$, wherein x is as appropriate for compounds of formula (I), employing a reagent such as borane in a suitable solvent, for example THF. The hydroxyl may then be optionally protected, for example as a silyl ether, and this intermediate converted into a compound of formula (I) in which $R^1$, or $R^{2a}$ or $R^{2b}$ is a protected hydroxyalkyl group, by one of the methods described above.

Compounds of formula (VIII) may be prepared by the reduction of a compound of formula (IX) to the corresponding amine, for example using hydrogenation in the presence of a suitable catalyst such as palladium on carbon.

Certain compounds of formula (IX) wherein the group L comprises of a fragment represented by $—O(CH_2)_{1-5}—$ may be obtained by the reaction of a compound of formula (XIIa), wherein X and $R^3$ are as defined for compounds of formula (I)

$$HO—(CH_2)_{1-5}—X—NHR^3 \quad (XIIa)$$

and a compound of formula (XIII):

$$O_2N—Ar—OH \quad (XIII)$$

wherein Ar is as defined above for compounds of formula (I), for example under Mitsunobu coupling conditions, typically in the presence of a triarylphosphine such as triphenylphosphine and a dialkyl azodicarboxylate such as diisopropylazodicarboxylate. The reaction is suitably carried out in a polar aprotic solvent such as THF.

Alternatively, certain compounds of formula (IX) wherein the group L comprises of a fragment represented by $—O(CH_2)_{1-5}—$ may be obtained by a nucleophilic aromatic substitution ($S_NAr$) reaction of a compound of formula (XIIa) with a compound of (XIV)

$$O_2N—Ar—Z \quad (XIV)$$

wherein Ar is as defined above for compounds of formula (I) and Z is a halogen atom, most preferably fluorine. The reaction is conveniently conducted in the presence of a strong base such as sodium hydride and in an aprotic solvent such as THF.

Certain compounds of formula (IX) wherein the group L is O, that is an oxa linker, may be obtained by the reaction of a compound of formula (XIIb), wherein X and $R^3$ are as defined for compounds of formula (I)

$$HO—X—NHR^3 \quad (XIIb)$$

and a compound of formula (XIV). The reaction may be conducted in the presence of an organic base such DBU in a polar aprotic solvent such as acetonitrile.

Certain compounds of formula (IX) wherein the group L is O, that is an oxa linker, may be obtained by the reaction of a compound of formula (XIIc), wherein X and $R^3$ are as defined for compounds of formula (I) and Y is a halogen atom preferably chlorine $$Y—X—NHR^3 \quad (XIIc)$$

and a compound of formula (XIII). The reaction may be effected in a polar aprotic solvent, such as NMP, in the presence of a strong mineral acid, such conc. hydrochloric acid and at an elevated temperature for example at 170° C. to 190° C.

Certain compounds of formula (VII) wherein the group L is O, that is an oxa linker, may be obtained via the reaction of a compound of formula (XIId),

(XIId)

wherein X, $R^3$ and $R^4$ are as defined for compounds of formula (I) with a compound of formula (XIV) providing compounds of formula (XV).

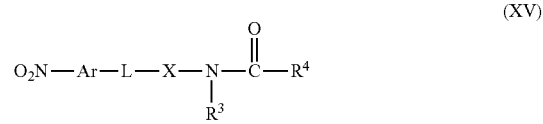

(XV)

Compounds of formula (VII) are revealed from compounds of formula (XV) by the reduction of the nitroarene to the corresponding amine. This transformation may be conducted by catalytic hydrogenation in a suitable solvent mixture such as a mixture of DCM, MeOH and acetic acid, over an appropriate metal catalyst, for example platinum supported on graphite, at RT. Alternatively it may be advantageous to conduct the reduction step by chemical means, for example using a metal such as iron powder, in an acid, such as glacial acetic acid at an elevated temperature, such as 60° C.

Certain compounds of formula (I) wherein Ar, X, $R^1$, and $R^3$ are as previously defined above and the group L is S, that is a thio ether linker; may be prepared from a compound of formula (IIb), by the processes described above for a compound of formula (II) A compound of formula (IIb) may be obtained from a compound of formula (VIII) wherein Ar, $R^3$ and X are as defined above and L is S; by reaction with a compound of formula (VIa) or a compound of formula (VIb) as described above.

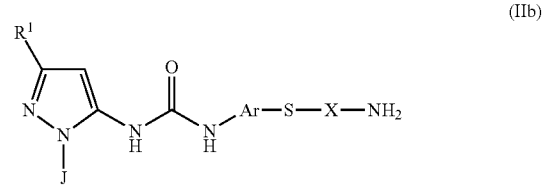

(IIb)

Compounds of formula (VIII) wherein $R^3$, Ar, J and X are as defined above and L is S, that is L is a thioether linker, may be prepared from a compound of formula (VIIIc) wherein the group $Ar^1$ is a leaving group with an electron rich aromatic nucleus, thereby making the radical —CH$_2$Ar$^1$ susceptible to cleavage by acidolysis. A suitable aromatic group for this purpose is, for example 2,4-dimethoxybenzene and the like. The desired compound of formula (VIII), as defined above, may be obtained from the compound of formula (VIIIc) by acid mediated cleavage, for example with hydrochloric acid in an alcoholic solvent such methanol, at an elevated temperature such as at reflux:

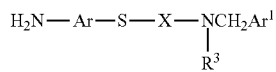
(VIIIc)

Compounds of formula (VIIIc) are obtainable from the reaction of a compound of formula (XVI) wherein Ar and X are as defined above and Y is a halogen atom, preferably chlorine, with a compound of formula (XVII), wherein R$^3$ and Ar$^1$ are as defined above. The reaction may be carried out by heating the compound of formula (XVII) as a solution in the neat amine of formula (XVII) at a suitable temperature, such as 120° C.:

H$_2$N—Ar—S—X—Y (XVI)

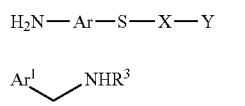
(XVII)

wherein X, Y, Ar$^1$ and R$^3$ are defined above.

Compounds of formula (XVI) may be prepared by reduction of compounds of formula (XVIII), for example by catalytic reduction using hydrogen and a suitable metal catalyst. The reduction step is conveniently carried out in a mixture of solvents such as EtOAc, MeOH and AcOH, over platinum on carbon, at an elevated temperature such as 50° C.

O$_2$N—Ar—S—X—Y (XVIII)

Compounds of formula (XVIII) may be prepared by the reaction of compounds of formula (XIV), as defined above, with a compound of formula (XIX)

Z—X—Y (XIX)

wherein X is as defined above, Z is a halogen atom, preferably fluorine and Y is a halogen atom, preferably chlorine together with a suitable sulfur nucleophile. For example the reaction can be carried using sodium hydrogensulfide as the sulfur source in a polar aprotic solvent such as DMF and in the presence of a organic base, for example DIPEA, at ambient temperature.

Certain compounds of formula (I) wherein, R$^1$, R$^{2a}$, R$^{2b}$, Ar and X are as previously defined, R$^3$ is H and L is SO$_2$, that is L is a sulfonyl linker, may be prepared from a compound of formula (IIc) by one or more of the processes described above.

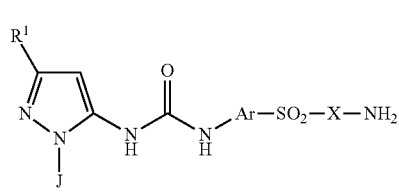
(IIc)

Compounds of formula (IIc) can be derived from a compound of formula (XX),

H$_2$N—Ar—SO$_2$—X—NHP$^1$ (XX)

OCN—Ar—SO$_2$—X—NHP$^1$ (XXI)

wherein Ar, X and P$^1$ are as previously defined, by conversion, in situ, into an isocyanate of formula (XXI) followed by, without isolation, reaction with a compound of formula (V). The transformation may be effected by exposing the compound of formula (XX) to a compound of formula (IVb); wherein, for example, the group LG$_3$ is halogen such as chlorine and the group LG$_4$ is trihalomethoxy such as trichloromethoxy, such that the compound of formula (IVb) is diphosgene, and subsequently of admixing the compound of formula (V). The reaction is conveniently conducted in an inert aprotic solvent such as DCM and may be cooled, for example to 0° C. The desired compounds of formula (IIc) are then revealed from the products so obtained by a deprotection step. For example, where P$^1$ represents a Boc group the compounds of formula (IIc) are obtained following removal of the protective group with an acid such as TFA, in an inert solvent such as DCM, conveniently at 0° C. to RT.

Compounds of formula (XX), wherein Ar, X and P$^1$ are as previously defined, may be obtained by the reduction of compounds of formula (XXII).

O$_2$N—Ar—SO$_2$—X—NHP$^1$ (XXII)

The reduction may be carried out, for example, by hydrogenation over a suitable catalyst, such as palladium on carbon, in an appropriate solvent system such as a mixture of EtOAc, MeOH and AcOH, and if necessary with warming, for example at 30° C.

Compounds of formula (XXII) are accessible from compounds of formula (XVIIa)

O$_2$N—Ar—SO$_2$—X—Y (XVIIIa)

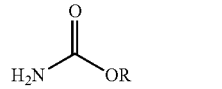
(XXIII)

wherein Ar and X are as previously defined above and Y is a halogen atom, preferably chlorine, by an amidation reaction employing a compound of formula (XXIII). A suitable compound of formula (XXIII) for this transformation is that in which R represents tert-butyl such that the said compound (XXIII) is H$_2$NC(O)O$^t$Bu. Suitable conditions for this conversion are, for example, the reaction of a compound of formula (XVIIIa) with a compound of formula (XXV) in the presence of a catalytic system, such as that generated from Pd$_2$(dba)$_3$ in the presence of the phosphine ligand such as XantPhos. The reaction is conveniently conducted in a polar aprotic solvent such as THF and in the presence of a base, for example, an inorganic base such as cesium carbonate.

Compounds of formula (XVIIIa) wherein Ar is as previously defined and X is pyridine may be derived from a compound of formula (XXIV):

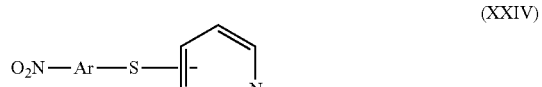
(XXIV)

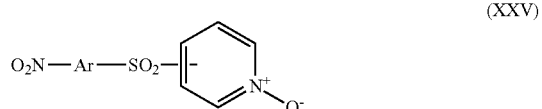
(XXV)

by oxidation to a compound of formula (XXV) followed by treatment with a chlorinating agent. A suitable oxidising reagent for the conversion of a compound of formula (XXIV) into a compound of formula (XXV) is, for example, m-CPBA. The reaction may be effected in a halogenated solvent such as DCM and typically below RT, for example at 0° C. The subsequent chlorination step may be carried out using a reagent such as phosphorus oxychloride at an elevated temperature, for example at 100° C.

Compounds of formula (XXIV) may be obtained from the reaction of a compound of formula (XIV) as defined previously, with a compound of formula (XXVI):

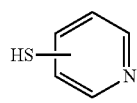

(XXVI)

The reaction is conveniently conducted in a polar aprotic solvent such as DMF and typically in the presence of a base, for example an inorganic base such as potassium carbonate, and if necessary with cooling, for example, to 0° C.

Compounds of formulae (III), (IVa), (IVb), (V), (X), (XI), (XIIa), (XIIb), (XIIc), (XIII), (XIV), (XVII), (XIX), (XXIII), (XXVI) and certain other compounds illustrated in the schemes are either commercially available, or were obtained using the cited procedures, or can be readily prepared by conventional methods by those skilled in the art. See for example Regan, J. et al.: *J. Med. Chem.*, 2003, 46, 4676-4686, WO00/043384, WO2007/087448 and WO2007/089512.

Protecting groups may be required to protect chemically sensitive groups during one or more of the reactions described above, to ensure that the process is efficient. Thus if desired or necessary, intermediate compounds may be protected by the use of conventional protecting groups. Protecting groups and means for their removal are described in "Protective Groups in Organic Synthesis", by Theodora W. Greene and Peter G. M. Wuts, published by John Wiley & Sons Inc; 4$^{th}$ Rev Ed., 2006, ISBN-10: 0471697540.

Novel intermediates are claimed as an aspect of the invention.

In one aspect the compounds are useful in treatment, for example COPD and/or asthma.

The p38MAPK inhibitory compounds developed to date have typically been intended for oral administration. This method of dosing involves optimization to achieve an adequate duration of action by selecting compounds that have an appropriate pharmacokinetic profile. This strategy ensures that a therapeutically effective drug concentration is established and maintained after and between doses to provide the desired clinical benefit. The inevitable consequence of this regimen is that all body tissues, especially liver and gut, are likely to be exposed chronically to therapeutically active concentrations of the drug, whether or not they are adversely affected in the diseased state.

An alternative strategy is to design treatment approaches in which the drug is dosed directly to the inflamed organ (topical therapy). While this approach is not suitable for treating all chronic inflammatory diseases, it has been extensively exploited in lung diseases (asthma, COPD), skin diseases (atopic dermatitis and psoriasis), nasal diseases (allergic rhinitis) and gastrointestinal diseases (ulcerative colitis).

In topical therapy, efficacy can be achieved either by ensuring that the drug has a sustained duration of action and is retained in the relevant organ to minimize the risk of systemic toxicity; or by producing a formulation which generates a "reservoir" of the active drug which is available to sustain the drug's desired effects. The first approach is exemplified by the anticholinergic drug tiotropium (Spiriva). This compound is administered topically to the lung as a treatment for COPD, and has an exceptionally high affinity for its target receptor resulting in a very slow off rate and a consequent sustained duration of action.

There is provided according to one aspect of the present disclosure use of a compound of formulation as a p38 MAP kinase inhibitor, for example administered topically to the lung.

In one aspect of the disclosure the compounds herein are particularly suitable for topical delivery, such as topical delivery to the lungs, in particular for the treatment of COPD.

Thus is one aspect there is provided use of compounds of formula (I) for the treatment of COPD and/or asthma, in particular COPD or severe asthma, by inhalation i.e. topical administration to the lung. Advantageously, administration to the lung allows the beneficial effects of the compounds to be realised whilst minimising the side-effects for patients.

In one aspect the compounds have a longer duration of actions than BIRB 796.

In one embodiment the compounds are suitable for sensitizing patients to treatment with a corticosteroid.

The compounds herein may also be useful for the treatment of rheumatoid arthritis.

Further, the present invention provides a pharmaceutical composition comprising a compound according to the disclosure optionally in combination with one or more pharmaceutically acceptable diluents or carriers.

Diluents and carriers may include those suitable for parenteral, oral, topical, mucosal and rectal administration.

As mentioned above, such compositions may be prepared e.g. for parenteral, subcutaneous, intramuscular, intravenous, intra-articular or peri-articular administration, particularly in the form of liquid solutions or suspensions; for oral administration, particularly in the form of tablets or capsules; for topical e.g. pulmonary or intranasal administration, particularly in the form of powders, nasal drops or aerosols and transdermal administration; for mucosal administration e.g. to buccal, sublingual or vaginal mucosa, and for rectal administration e.g. in the form of a suppository.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like.

Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

Compositions suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrollidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitably the compound of formula (I) is administered topically to the lung. Hence we provide according to the invention a pharmaceutical composition comprising a compound of the disclosure optionally in combination with one or more topically acceptable diluents or carriers. Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser. Topical administration to the lung may also be achieved by use of a dry-powder formulation. A dry powder formulation will contain the compound of the disclosure in finely divided form, typically with a mass mean diameter (MMAD) of 1-10 microns. The formulation will typically contain a topically acceptable diluent such as lactose, usually of large particle size e.g. a mass mean diameter (MMAD) of 100 μm or more. Example dry powder delivery systems include SPINHALER, DISKHALER, TURBOHALER, DISKUS and CLICKHALER.

Compounds according to the disclosure are intended to have therapeutic activity. In a further aspect, the present invention provides a compound of the disclosure for use as a medicament.

Compounds according to the disclosure may also be useful in the treatment of respiratory disorders including COPD (including chronic bronchitis and emphysema), asthma, paediatric asthma, cystic fibrosis, sarcoidosis, idiopathic pulmonary fibrosis, allergic rhinitis, rhinitis, sinusitis, especially asthma, chronic bronchitis and COPD.

Compounds of the disclosure may also re-sensitise the patient's condition to treatment with a corticosteroid, when the patient's condition has become refractory to the same.

Compounds according to the disclosure are also expected to be useful in the treatment of certain conditions which may be treated by topical or local therapy including allergic conjunctivitis, conjunctivitis, allergic dermatitis, contact dermatitis, psoriasis, ulcerative colitis, inflamed joints secondary to rheumatoid arthritis or osteoarthritis.

Compounds of the disclosure are also expected to be useful in the treatment of certain other conditions including rheumatoid arthritis, pancreatitis, cachexia, inhibition of the growth and metastasis of tumours including non-small cell lung carcinoma, breast carcinoma, gastric carcinoma, colorectal carcinomas and malignant melanoma.

Compounds of the disclosure are believed to be useful as anti-viral agents, for example in the treatment of conditions including influenza. In particular the compounds of the present disclosure may be suitable for the use in the treatment or prevention of said viral infection and in particular may be capable of reducing viral load and/or ameliorating symptoms after infection.

Thus, in a further aspect, the present invention provides a compound as described herein for use in the treatment of the above mentioned conditions.

In a further aspect, the present invention provides use of a compound as described herein for the manufacture of a medicament for the treatment of the above mentioned conditions.

In a further aspect, the present invention provides a method of treatment of the above mentioned conditions which comprises administering to a subject an effective amount of a compound of the disclosure or a pharmaceutical composition thereof.

The word "treatment" is intended to embrace prophylaxis as well as therapeutic treatment.

A compound of the disclosure may also be administered in combination with one or more other active ingredients e.g. active ingredients suitable for treating the above mentioned conditions. For example possible combinations for treatment of respiratory disorders include combinations with steroids (e.g. budesonide, beclomethasone dipropionate, fluticasone propionate, mometasone furoate, fluticasone furoate), beta agonists (e.g. terbutaline, salbutamol, salmeterol, formoterol) and/or xanthines (e.g. theophylline).

EXPERIMENTAL SECTION

Abbreviations

Abbreviations used herein are as defined in the table below. Any abbreviations not defined are intended to convey their generally accepted meaning.
AcOH glacial acetic acid
aq aqueous
Ac acetyl
ATP adenosine-5'-triphosphate
BALF bronchoalveolae lavage fluid
9-BBN 9-borabicyclo[3.3.1]nonane
Boc tert-butoxycarbonyl
br broad
BSA bovine serum albumin
CatCart® catalytic cartridge
CBz benzyloxycarbonyl CDI 1,1-carbonyl-diimidazole
COPD chronic obstructive pulmonary disease
d doublet
DCM dichloromethane
DIAD diisopropylazadicarboxylate
DIBAL-H diisobutylaluminium hydride
DIPEA N,N-diisopropylethylamine
DMF N,N-dimethylformamide
DMSO dimethyl sulfoxide
EDC.HCl 1-ethyl-3-(3-dimethylaminopropyl)carbodiimide. hydrochloride
(ES$^+$) electrospray ionization, positive mode
Et ethyl
EtOAc ethyl acetate
FCS foetal calf serum
HOBt 1-hydroxybenzotriazole
hr hour(s)
HRP horseradish peroxidase
JNK c-Jun N-terminal kinase
KHMDS potassium hexamethyldisilazane
(M+H)$^+$ protonated molecule
MAPK mitogen protein activated protein kinase
Me methyl
MeCN acetonitrile
MeOH methanol
MHz megahertz
min minute(s)
MOM-Br bromomethyl methyl ether
MTT 3-(4,5-Dimethylthiazol-2-yl)-2,5-diphenyltetrazolium bromide
m/z: mass-to-charge ratio
NMM N-methylmorpholine; (4-methylmorpholine)
NMP 1-methylpyrrolidin-2-one (N-methyl-2-pyrrolidone)
NMR nuclear magnetic resonance (spectroscopy)
Oxone® potassium peroxymonosulfate
Ph phenyl
PBS phosphate buffered saline
Pd$_2$(dba)$_3$ tris(dibenzylideneacetone)dipalladium (0)
PPh$_3$ triphenylphosphine
PyBOP® (benzotriazol-1-yloxy)tripyrrolidinophosphonium hexafluorophosphate
q quartet
RT room temperature
RP HPLC reverse phase high performance liquid chromatography
s singlet
SCX solid supported cation exchange (resin)
SDS sodium dodecyl sulphate
S$_N$Ar nucleophilic aromatic substitution
t triplet
TBAF tetrabutylammonium fluoride
TBDMS-Cl tert-butyldimethylchlorosilane
TFA trifluoroacetic acid
THF tetrahydrofuran
TMB 3,3',5,5'-tetramethylbenzidine
TNFα tumor necrosis factor alpha
TMS-Cl trimethylsilyl chloride [chlorotrimethylsilane]
XantPhos 4,5-bis(diphenylphosphino)-9,9-dimethylxanthene General Procedures All starting materials and solvents were either obtained from commercial sources or prepared according to the literature citation. Unless otherwise stated all reactions were stirred. Organic solutions were routinely dried over anhydrous magnesium sulfate. Hydrogenations were preformed on a Thales H-cube flow reactor under the conditions stated.

Column chromatography was performed on pre-packed silica (230-400 mesh, 40-63 μM) cartridges using the amount indicated. SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% NH$_3$ in MeOH.

Preparative Reverse Phase High Performance Liquid Chromatography:

Agilent Scalar column C18, 5 μm (21.2×50 mm), flow rate 28 mL·min$^{-1}$ eluting with a H$_2$O-MeCN gradient containing 0.1% v/v formic acid over 10 min using UV detection at 215 and 254 nm. Gradient information: 0.0-0.5 min; 95% H$_2$O-5% MeCN; 0.5-7.0 min; ramped from 95% H$_2$O-5% MeCN to 5% H$_2$O-95% MeCN; 7.0-7.9 min; held at 5% H$_2$O-95% MeCN; 7.9-8.0 min; returned to 95% H$_2$O-5% MeCN; 8.0-10.0 min; held at 95% H$_2$O-5% MeCN.

Analytical Methods

Reverse Phase High Performance Liquid Chromatography:

Method 1: Agilent Scalar column C18, 5 μm (4.6×50 mm) or Waters XBridge C18, 5 μm (4.6×50 mm) flow rate 2.5 mL·min$^{-1}$ eluting with a H$_2$O-MeCN gradient containing either 0.1% v/v formic acid (Method 1 acidic) or NH$_3$ (Method 1 basic) over 7 min employing UV detection at 215 and 254 nm. Gradient information: 0.0-0.1 min, 95% H$_2$O-5% MeCN; 0.1-5.0 min, ramped from 95% H$_2$O-5% MeCN to 5% H$_2$O-95% MeCN; 5.0-5.5 min, held at 5% H$_2$O-95% MeCN; 5.5-5.6 min, held at 5% H$_2$O-95% MeCN, flow rate increased to 3.5 mL·min$^{-1}$; 5.6-6.6 min, held at 5% H$_2$O-95% MeCN, flow rate 3.5 mL·min$^{-1}$; 6.6-6.75 min, returned to 95% H$_2$O-5% MeCN, flow rate 3.5 mL·min$^{-1}$; 6.75-6.9 min, held at 95% H$_2$O-5% MeCN, flow rate 3.5 mL·min$^{-1}$; 6.9-7.0 min, held at 95% H$_2$O-5% MeCN, flow rate reduced to 2.5 mL·min$^{-1}$.

Method 2: Agilent Extend C18 column, 1.8 μm (4.6×30 mm) at 40° C.; flow rate 2.5-4.5 mL·min$^{-1}$ eluting with a H$_2$O-MeCN gradient containing 0.1% v/v formic acid over 4 min employing UV detection at 254 nm. Gradient information: 0-3.00 min, ramped from 95% H$_2$O-5% MeCN to 5% H$_2$O-95% MeCN; 3.00-3.01 min, held at 5% H$_2$O-95% MeCN, flow rate increased to 4.5 mL·min$^{-1}$; 3.01-3.50 min, held at 5% H$_2$O-95% MeCN; 3.50-3.60 min, returned to 95% H$_2$O-5% MeCN, flow rate reduced to 3.50 mL·min$^{-1}$; 3.60-3.90 min, held at 95% H$_2$O-5% MeCN; 3.90-4.00 min, held at 95% H$_2$O-5% MeCN, flow rate reduced to 2.5 mL·min$^{-1}$.

$^1$H NMR Spectroscopy:

Bruker Avance III 400 MHz using residual undeuterated solvent as reference

COMPOUND EXAMPLES 1-(3-tert-Butyl-1-p-tolyl-1H-pyrazol-5-yl)-3-(4-(2-morpholinethoxy)naphthalen-1-yl)urea: BIRB 796

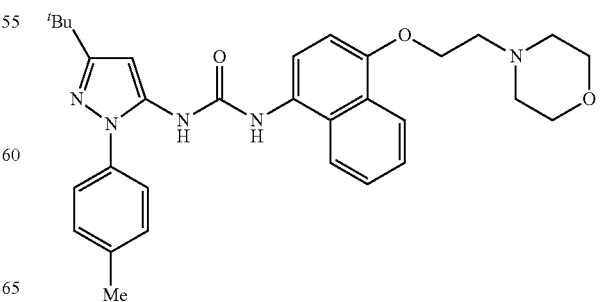

A sample of BIRB 796 was prepared according to the published procedure: Cirillo, P. F., Gilmore, T. A., Hickey, E., Regan, J. and Zhang, L. H. Aromatic Heterocyclic Compounds as Antiinflammatory Agents, WO 00/43384 (27 Jul. 2000).

Intermediate A 3-tert-Butyl-1-p-tolyl-1H-pyrazol-5-amine

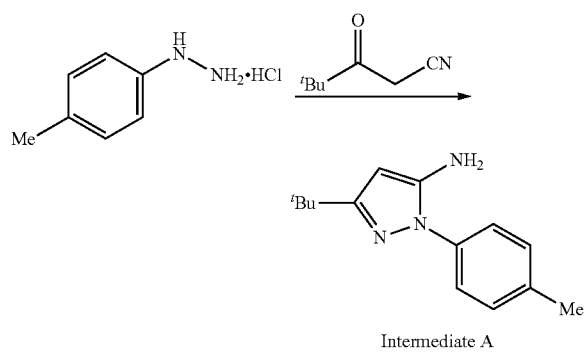

Intermediate A

The aminopyrazole Intermediate A1 was prepared by the condensation of p-tolylhydrazine hydrochloride and 4,4-dimethyl-3-oxopentanenitrile according to the published procedure: Cirillo, P. F. et al., WO 2000/43384, 27 Jul. 2000.

Intermediate B

N-(4-(2-(4-Aminonaphthalen-1-yloxy)ethyl)pyridin-2-yl)acetamide

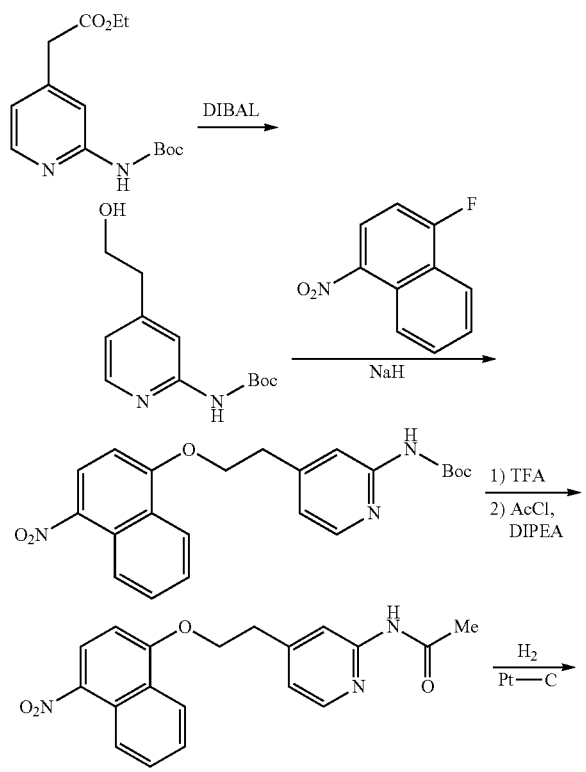

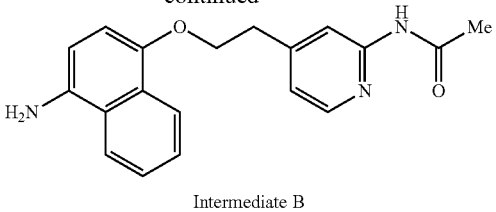

Intermediate B

To a solution of ethyl 2-(2-(tert-butoxycarbonylamino)pyridin-4-yl)acetate (WO 2007089512) (10.0 g, 35.7 mmol) under $N_2$ in THF (100 mL), at −78° C., was added a solution of DIBAL in THF (1.0M, 71.0 mL, 71.0 mmol) over 1 hr. The reaction mixture was stirred at −78 to −60° C. for 40 min and was then warmed to −15° C. over 1 hr. The solution was re-cooled to −78° C. and was treated with a further aliquot of DIBAL solution (36.0 mL, 36.0 mmol) and was allowed to warm to −40° C. and stirred for 1 hr. The reaction was quenched by the cautious addition of water (10 mL), followed $MgSO_4$. The solids were removed by filtration and the filtrate was evaporated in vacuo. The residue was purified by flash column chromatography ($SiO_2$, 330 g, EtOAc in hexanes, 65% v/v, isocratic elution) to give tert-buty 4-(2-hydroxyethyl)pyridin-2-ylcarbamate, (6.0 g, 64%) as a yellow solid: m/z 239 $(M+H)^+$ $(ES^+)$.

To a solution of tert-butyl 4-(2-hydroxyethyl)pyridin-2-ylcarbamate (6.0 g, 25 mmol) in THF (70 mL) at 0° C. was added sodium hydride (2.52 g, 60% wt dispersion in mineral oil, 63.0 mmol) and the bright yellow suspension stirred for 20 min and then treated with 1-fluoro-4-nitronaphthalene (4.81 g, 25.2 mmol) in a single portion. After stirring at RT for 2 hr the mixture was treated with water (100 mL) followed by EtOAc (100 mL) and the solid which formed at the interface was collected by filtration. The organic phase was separated and was washed with saturated aq. $NaHCO_3$ and brine and was then dried and evaporated in vacuo to furnish an orange solid. The two solids were combined and triturated with MeOH (50 mL) to provide tert-butyl 4-(2-(4-nitronaphthalen-1-yloxy)ethyl)pyridin-2-ylcarbamate, as a yellow solid (11.0 g, 98%): m/z 410 $(M+H)^+$ $(ES^+)$.

To a suspension of tert-butyl 4-(2-(4-nitronaphthalen-1-yloxy)ethyl)pyridin-2-ylcarbamate (900 mg, 2.20 mmol) in DCM (10.0 mL) was added TFA (10.0 mL) and the reaction mixture was stirred at RT overnight. The resulting mixture was evaporated in vacuo and the residue subjected to SCX capture and release. The crude product so obtained was taken up into THF (8.0 mL) and DIPEA (660 µl, 3.8 mmol) and then acetyl chloride (147 µl, 2.06 mmol) were added. After stirring for 1 hr, the mixture was diluted with saturated aq. $NaHCO_3$ (10.0 mL) and was extracted with EtOAc (2×20 mL). The combined organic layers were washed with brine and then dried, and evaporated in vacuo. The residue was taken up in a mixture of acetonitrile and a solution of $NH_3$ in MeOH (7M, 1:1 v/v, 20 mL) and after 10 min was re-evaporated in vacuo. The residue was triturated with MeOH (10.0 mL) to afford N-(4-(2-(4-nitronaphthalen-1-yloxy)ethyl)pyridin-2-yl)acetamide, as a yellow solid (570 mg, 74%): m/z 352 $(M+H)^+$ $(ES^+)$.

A solution of N-(4-(2-(4-nitronaphthalen-1-yloxy)ethyl)pyridin-2-yl)acetamide (570 mg, 1.62 mmol) in a mixture of AcOH: MeOH (6:1 v/v, 54 mL) was subjected to hydrogenation by passage through a Thales H-cube (1 mL·min$^{-1}$, 30 mm, 10% Pt/C Cat-Cart, full $H_2$, 45° C.). The solvent was removed by evaporation in vacuo, and, the residue was subjected to SCX capture and release to furnish the title compound, Intermediate B, (550 mg, 100%): m/z 322 $(M+H)^+$ $(ES^+)$.

Intermediate C 1-(4-((2-aminopyridin-4-yl)methoxy)naphthalen-1-yl)-3-(3-tert-butyl-M-p-tolyl-1H-pyrazol-5-yl)urea

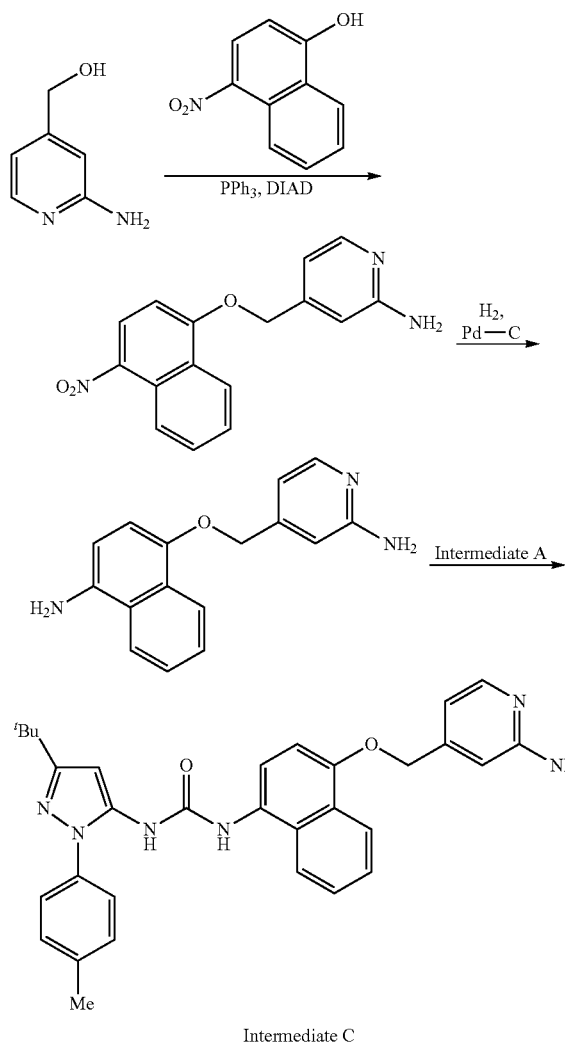

Intermediate C

To a solution of 4-nitronaphthol (5.17 g, 27.3 mmol), triphenylphosphine (10.75 g, 41.0 mmol) and 2-aminopyridine-4-methanol (5.09 g, 41.0 mmol) in THF (50 mL) at −15° C. was added dropwise DIAD (8.07 mL, 41.0 mmol) and the mixture then allowed to warm to RT and stirred overnight. The volatiles were removed in vacuo and the residue was triturated with EtOAc (150 mL), and the crude product was collected by filtration and washed with EtOAc (100 mL). A second trituration with MeOH (100 mL) gave 2-amino-4-((4-nitronaphthalen-1-yloxy)methyl)pyridine (4.54 g, 56%) as a yellow solid: m/z 296 (M+H)$^+$ (ES$^+$).

A solution of 2-amino-4-((4-nitronaphthalen-1-yloxy)methyl)pyridine (4.50 g, 15.24 mmol) in MeOH (200 mL) and AcOH (200 mL) was passed through a Thales H-cube (2.0 mL·min$^{-1}$, 40° C., 55 mm 10% Pt/C Cat-Cart, full hydrogen mode) and the volatiles were removed in vacuo. The crude product was subjected to SCX capture and release and the solvent was removed in vacuo to give 2-amino-4-((4-aminonaphthalen-1-yloxy)methyl)pyridine, (3.82 g, 94%) as a purple solid: m/z 266 (M+H)$^+$ (ES$^+$).

A solution of CDI (4.18 g, 25.8 mmol) in DCM (15 mL) was added dropwise under nitrogen to a solution of Intermediate A (5.91 g, 25.8 mmol) in DCM (15 mL) over 40 min. The resulting solution was stirred at RT for 1 hr and was then added dropwise under nitrogen to a solution of 2-amino-4-((4-aminonaphthalen-1-yloxy)methyl)pyridine (3.80 g, 12.9 mmol) in DCM and the mixture was stirred overnight. The volatiles were removed in vacuo. and the residue was purified by flash column chromatography (SiO$_2$, 120 g, MeOH in DCM, 0-6%, gradient elution) to give the tite compound, Intermediate C, as an off white solid (4.27 g, 63%): m/z 521 (M+H)$^+$ (ES$^+$).

Intermediate D 1-(4-(2-Aminopyridin-4-yloxy)naphthalen-1-yl)-3-(3-tert-butyl-1-p-toly-1H-pyrazol-5-yl)urea

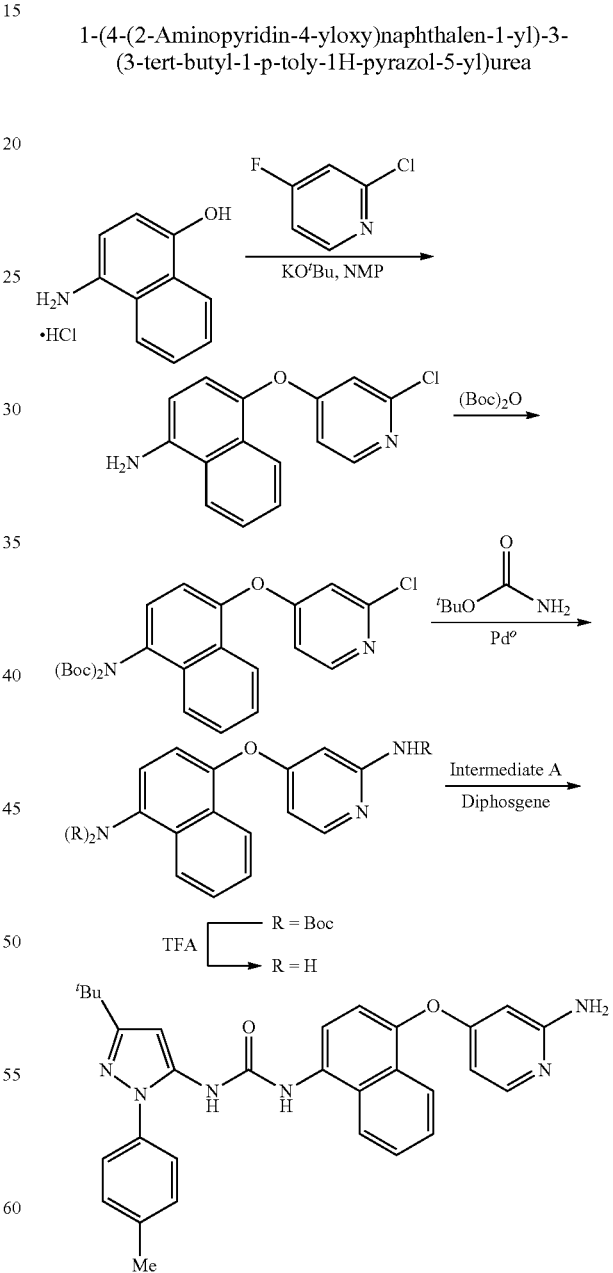

Intermediate D

To a stirred solution of 2-chloro-4-fluoropyridine (1.26 g, 9.58 mmol) and 4-amino-1-naphthol hydrochloride (750 mg, 3.83 mmol) in NMP (40 mL) at −20° C. was added potassium tert-butoxide (1.29 g, 11.50 mmol) and the reaction mixture was warmed to RT for 2.5 hr. The mixture was diluted with water (100 mL) and extracted with EtOAc (100 mL and 2×80 mL) and the combined organic extracts were washed with brine (150 mL), dried and evaporated in vacuo. The crude product was subjected to SCX capture and release and the volatiles were removed in vacuo to give 4-(2-chloropyridin-4-yloxy)naphthalen-1-amine as a brown solid (1.02 g, 92%): m/z 271 (M+H)+ (ES+).

To a stirred solution of 4-(2-chloropyridin-4-yloxy)naphthalen-1-amine (1.02 g, 3.76 mmol) in THF (30 mL) at 0° C. was added DMAP (34 mg, 0.282 mmol) and then di-tert-butyl dicarbonate (904 mg, 4.14 mmol). The reaction mixture was stirred at 0° C. for 30 min and was then allowed to warm to RT. After 1.5 hr the mixture was re-cooled to 0° C. and an additional aliquot of di-tert-butyl dicarbonate (904 mg, 4.14 mmol) was added. The resulting mixture was stirred at 0° C. for 15 min and at RT for 16 hr and was diluted with water (40 mL) and extracted with EtOAc (2×40 mL). The combined organic extracts were washed with brine (75 mL), dried and evaporated in vacuo. The residue was purified by flash column chromatography (SiO$_2$, 80 g, 0-40% EtOAc in iso-hexane, gradient elution) to give 4-(2-chloropyridin-4-yloxy)naphthalen-1-N,N-di-tert-butylcarbamate as a purple solid (892 mg, 48%): m/z 471 (M+H)+ (ES+).

A mixture of 4-(2-chloropyridin-4-yloxy)naphthalen-1-N,N-di-tert-butylcarbamate (892 mg, 1.89 mmol), tert-butyl carbamate (666 mg, 5.68 mmol), caesium carbonate (926 mg, 2.84 mmol), Pd$_2$(dba)$_3$ (43 mg, 0.047 mmol) and XantPhos (55 mg, 0.095 mmol) was suspended in THF (10.0 mL) and was purged thoroughly with nitrogen and then heated to reflux for 15 hr. The mixture was cooled to RT and diluted with water (35 mL) and was extracted with EtOAc (35 mL and 25 mL). The combined organic extracts were washed with brine (50 mL), dried and evaporated in vacuo. The residue was purified by flash column chromatography (SiO$_2$, 80 g, 0-30% EtOAc in iso-hexane, gradient elution) to give tert-butyl 4-(4-(N,N-di-(tert-butyloxy carbonyl)amino)naphthalen-1-yloxy)pyridin-2-yl carbamate, as a white solid (289 mg, 28%): m/z 552 (M+H)+ (ES+).

To a stirred solution of tert-butyl 4-(4-(N,N-di-(tert-butyloxycarbonyl)amino)naphthalen-1-yloxy)pyridin-2-yl carbamate (289 mg, 0.524 mmol) in DCM (8.0 mL), at 0° C., was added TFA (4.0 mL) and the resulting mixture allowed to warm to RT. After 5 hr the volatiles were removed in vacuo and the residue was taken up in MeOH (5.0 mL) and subjected to SCX capture. The volatiles were removed in vacuo to provide 4-(4-aminonaphthalen-1-yloxy)pyridin-2-amine, (116 mg, 85%) as a brown-orange oil: m/z 252 (M+H)+ (ES+).

To a vigorously stirred mixture of Intermediate A (206 mg, 0.900 mmol) in DCM (20 mL) and saturated aq. NaHCO$_3$ (14 mL) at 0° C. was added trichloromethylchloroformate (325 μL, 2.70 mmol) in a single portion and the stirring continued at 0° C. for 80 min. The organic layer was separated and dried and was evaporated in vacuo to provide 3-tert-butyl-5-isocyanato-1-p-tolyl-1H-pyrazole, as an orange oil. This material was pumped under high vacuum for 30 min and was then taken up into THF (6.0 mL) and the resulting solution kept under nitrogen at 0° C. for use in the next step.

To a stirred solution of 4-(4-aminonaphthalen-1-yloxy)pyridin-2-amine, (116 mg, 0.462 mmol) and DIPEA (240 μl, 1.39 mmol) in THF (3.0 mL) at 0° C. was added an aliquot of the isocyanate solution prepared above (2.0 mL, 0.300 mmol) and the resulting mixture allowed to warm to RT. Additional aliquots of the isocyanate solution were added to the reaction mixture after 1.5 hr, (1.0 mL, 0.150 mmol) and after a further 3.5 hr (0.5 mL, 0.075 mmol). The mixture was maintained at RT for 20 hr and was then diluted with water (30 mL) and was extracted with EtOAc (2×30 mL). The combined organic extracts were washed with brine (50 mL), dried and then evaporated in vacuo. The residue was purified by flash column chromatography (SiO$_2$; 12 g, 25-100% [5% MeOH in EtOAc] in iso-hexane, gradient elution) to furnish the title compound Intermediate D, as a brown oil (127 mg, 49%): m/z 507 (M+H)+ (ES+).

Example 1

N-(4-(2-(4-(3-(3-tert-Butyl-1-p-tolyl-1H-pyrazol-5-yl)ureido)naphthalen-1-yloxy)ethyl)pyridin-2-yl)acetamide

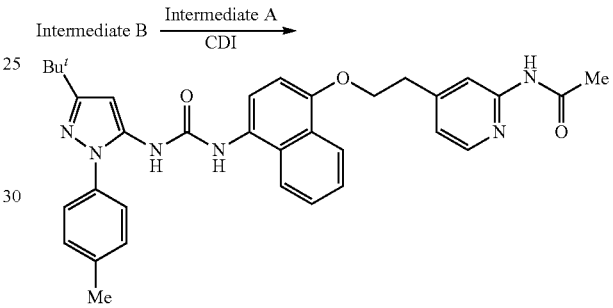

Example 1

To a suspension of CDI (416 mg, 2.57 mmol) in DCM (1.0 mL) was added a solution of Intermediate A (589 mg, 2.57 mmol) in DCM (2.0 mL) over 1.5 hr and after 1 hr a solution of Intermediate B (550 mg, 1.711 mmol) in DCM (6.0 mL) was added and the reaction mixture maintained at RT for 16 hr. The reaction mixture was loaded directly on to silica and was purified by flash column chromatography (SiO$_2$, 40 g, EtOAc in isohexane, 50-100%, gradient elution) to afford the title compound, Example 1, (700 mg, 71%): m/z 577 (M+H)+ (ES+). $^1$H NMR (400 MHz, DMSO-dr) δ: 1.26 (9 H, s), 2.08 (3 H, s), 2.38 (3 H, s), 3.20 (2H, t), 4.37 (2H, t), 6.34 (1H, s), 6.95 (1H, d), 7.15 (1H, dd), 7.35 (2H, m), 7.45 (3H, overlapping m), 7.55 (1H, m), 7.60 (1H, m), 7.90 (1H, d), 8.20 (3H, overlapping m), 8.57 (1H, s), 8.77 (1H, s) and 10.40 (1H, s).

Example 2

N-(4-(((4-(3-(3-(tert-Butyl)-1-(p-tolyl)-1H-pyrazol-5-yl)ureido)naphthalen-1-yl)oxy)methyl)pyridin-2-yl)acetamide

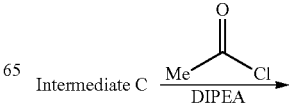

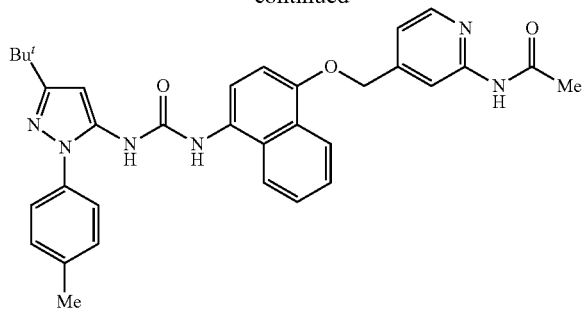

Example 2

To a mixture of Intermediate C (40 mg, 0.08 mmol) and DIPEA (15 µL, 0.09 mmol) in DCM/DMF (10:1, 1.1 mL) was added acetyl chloride (6 µL, 0.08 mmol). After stirring for 40 min RT, further DIPEA (15 µL, 0.09 mmol) and acetyl chloride (6 µL, 0.08 mmol) were added sequentially and stirring was continued for 30 min. The reaction mixture was diluted with AcOH and subjected to purification by SCX capture and release. The crude product so obtained was triturated with DCM to afford the title compound, Example 2, as a pale orange solid (21 mg, 50%); $R^1$ 3.86 min (Method 1 basic); m/z 563 (M+H)$^+$ (ES$^+$). $^1$H NMR (400 MHz, DMSO-d$_6$) δ: 1.29 (9 H, s), 2.10 (3H, s), 2.39 (3 H, s), 5.36 (2H, s), 6.35 (1H, s), 7.01 (1H, d), 7.23 (1H, dd), 7.36 (2H, d), 7.44 (2H, d), 7.57-7.63 (3H, overlapping m), 7.92 (1H, m), 8.29-8.33 (3H, overlapping m), 8.59 (1H, s), 8.79 (1H, s), 10.53 (1H, s).

Example 3

N-(4-((4-(3-(3-(tert-Butyl)-1 (p-tolyl)-1H-pyrazol-5-yl)ureido)naphthalen-1-yl)oxy)pyridin-2-yl)acetamide

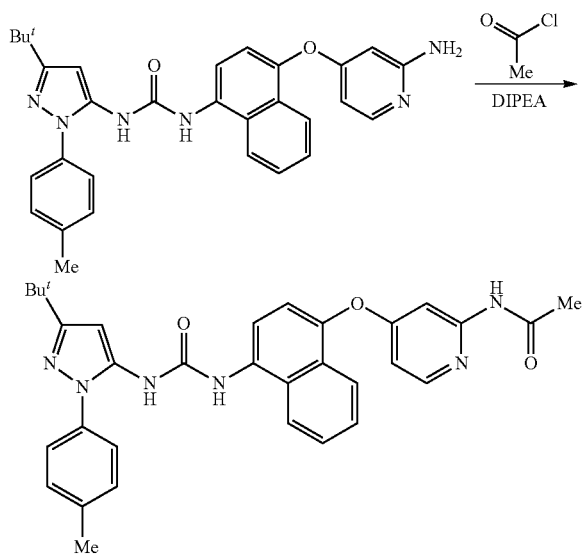

Example 3

To a mixture of 1-(4-(2-aminopyridin-4-yloxy)naphthalen-1-yl)-3-(3-tert-butyl-1-p-tolyl-1H-pyrazol-5-yl)urea (40 mg, 0.08 mmol) and DIPEA (69 µL, 0.40 mmol) in THF (5.0 mL) at 0° C. under N$_2$ was added acetyl chloride (22 µL, 0.08 mmol) and the mixture maintained at 0° C. for 30 min and then warmed to RT for 16 hr. The reaction was quenched by the addition of a solution of NH$_3$ in MeOH (1% w/v, 2.0 mL) and after 45 min at RT the volatiles were evaporated in vacuo. The residue was subjected to purification by SCX capture and release and then by flash column chromatography (SiO$_2$, 12 g, [5% MeOH in EtOAc] in isohexane, 0-70%, gradient elution). The impure material so obtained was subjected to re-purification by SCX capture and release and by flash column chromatography (SiO$_2$, 12 g, [5% MeOH in EtOAc] in isohexane, 0-65%, gradient elution) to afford the title compound, Example 3, as a white solid (12 mg, 27%); $R^1$ 2.26 min (Method 2); m/z 549 (M+H)$^+$ (ES$^+$). $^1$H NMR (400 MHz, DMSO-d$_6$) δ: 1.29 (9 H, s), 2.01 (3H, s), 2.38 (3 H, s), 6.39 (1H, s), 6.63 (1H, dd), 7.31 (1H, d), 7.36 (2H, d), 7.48 (2H, d), 7.56 (1H, m), 7.61-7.66 (2H, overlapping m), 7.83 (1H, d), 7.96 (1H, d), 8.16 (1H, d), 8.19 (1H, d), 9.02 (1H, s), 9.30 (1H, s), 10.52 (1H, s).

Biological Testing: Experimental Methods

Enzyme Inhibition Assay

The enzyme inhibitory activities of compounds disclosed herein were determined by fluorescence resonance energy transfer (FRET) using synthetic peptides labelled with both donor and acceptor fluorophores (Z-LYTE, Invitrogen Ltd., Paisley, UK). Recombinant, phosphorylated p38 MAPKγ (MAPK12:Invitrogen) was diluted in HEPES buffer, mixed with the test compound at the desired final concentrations and incubated for 2 hr at RT. The FRET peptide (2 µM) and ATP (100 µM) were added to the enzyme/compound mixture and incubated for 1 hr. Development reagent (protease) was added for 1 hr prior to detection in a fluorescence microplate reader (Varioskan® Flash, ThermoFisher Scientific). The site-specific protease cleaves non-phosphorylated peptide only and eliminates the FRET signal. Phosphorylation levels of each reaction were calculated using the ratio of coumarin emission (donor) over fluorescein emission (acceptor) for which high ratios indicate high phosphorylation and low ratios indicate low phosphorylation levels. The percentage inhibition of each reaction was calculated relative to non-inhibited control and the 50% inhibitory concentration (IC$_{50}$ value) then calculated from the concentration-response curve.

For the p38 MAPKα isoform (MAPK14: Invitrogen), enzyme activity was evaluated indirectly by determining the level of activation/phosphorylation of the down-stream molecule, MAPKAP-K2. The p38 MAPKα protein was mixed with the test compound for 2 hr at RT. The p38α inactive target MAPKAP-K2 (Invitrogen) and FRET peptide (2 µM), which is a phosphorylation target for MAPKAP-K2, and ATP (10 µM) were then added to the enzymes/compound mixture and the resulting mixture incubated for 1 hr. Development reagent was then added and the mixture incubated for 1 hr before detection by fluorescence completed the assay protocol.

Cellular Potency Assays:

1) LPS-Induced TNFα/IL-8 Release in d-U937Cells

U937 cells, a human monocytic cell line, were differentiated to macrophage-type cells by incubation with phorbol myristate acetate (PMA; 100 ng/ml) for 48 to 72 hr. Cells were pre-incubated with final concentrations of test compound for 2 hr and were then stimulated with 0.1 µg/mL of LPS (from *E. Coli*: O111:B4, Sigma) for 4 hr. The supernatant was collected for determination of TNFα and IL-8 concentrations by sandwich ELISA (Duo-set, R&D systems). The inhibition of TNFα production was calculated as a percentage of that achieved by 10 µg/mL of BIRB796 at each concentration of test compound by comparison against vehicle control. The relative 50% effective concentration (REC$_{50}$) was determined from the resultant concentration-response curve. The inhibition of IL-8 production was calculated at each concentration of test compound by comparison with vehicle control. The 50% inhibitory concentration (IC$_{50}$) was determined from the resultant concentration-response curve.

2) LPS-Induced TNFα Release in THP-1 Cells

THP-1 cells, a human monocytic cell line, were stimulated with 3 μg/mL of LPS (from *E. Coli*: 0111:B4, Sigma) for 4 hr and the supernatant collected for determination of the TNFα concentration by sandwich ELISA (Duo-set, R&D systems). The inhibition of TNFα production was calculated at each concentration by comparison with vehicle control. The 50% inhibitory concentration (IC$_{50}$) was determined from the resultant concentration-response curve.

MTT Assay: Cell Viability

Differentiated U937 cells were pre-incubated with each test compound under two protocols: the first for 4 hr in 5% FCS and the second in 10% FCS for 24 h. The supernatant was replaced with 200 μL of new media and 10 μL of MTT stock solution (5 mg/mL) was added to each well. After incubation for 1 hr the media were removed, 200 μL of DMSO was added to each well and the plates were shaken lightly for 1 hr prior to reading the absorbance at 550 nm. The percentage loss of cell viability was calculated for each well relative to vehicle (0.5% DMSO) treatment. Consequently an apparent increase in cell viability for drug treatment relative to vehicle is tabulated as a negative percentage.

The in vitro profiles of the compound examples disclosed herein, as determined using the protocols described above, are presented below (Table 1).

TABLE 1

In Vitro Profiles of Compound Examples

| | | | | | Cellular Profiles | | | | |
|---|---|---|---|---|---|---|---|---|---|
| | | | | | LPS/TNFα | | LPS-IL8 | | |
| Example | Enzyme Inhibition IC$_{50}$ (nM) | | | | THP-1 IC$_{50}$ | REC$_{50}$ | d-U937 IC$_{50}$ | MTT Assay [a] | |
| No | p38α | p38γ | HCK | c-Src | (nM) | (nM) | (nM) | 4 h | 24 h |
| BIRB796 | 12 | 296 | NE[b] | NE[b] | 4.1 | 4.8 | NE[b] | − | − |
| 2 | 2.5 | 195 | NT | 166 | NT | 3.6 | NT | − | +[$] |
| 3 | 6.7 | 146 | NT | <18 | 1.6 | 1.0 | NT | − | + |

[a] Cell Viability Assay: + = >30% inhibition; − = <30% inhibition at 10 μg/ml; [$]= negative at 1 μg/ml;
[b] No effect at a concentration of 1 ug/ml 3) Poly I:C-Induced ICAM-1 Induction in BEAS2B Cells Poly I:C (1 μg/m) (Invivogene Ltd., San Diego, Calif.) was transfected into BEAS2B cells (human bronchial epithelial cells, ATCC) with Oligofectamine (Invitrogen, Carlsbad, Calif.). Cells were pre-incubated with final concentrations of test compounds for 2 hr and the level of ICAM1 expression on the cell surface was determined by cell-based ELISA. At a time point 18 hr after poly I:C transfection, cells were fixed with 4% formaldehyde in PBS. and then endogenous peroxidase was quenched by the addition of 0.1% sodium azide and 1% hydrogen peroxide. Cells were washed with wash-buffer (0.1% Tween in PBS: PBS-Tween). and after blocking the wells with 5% milk in PBS-Tween for 1 hr, the cells were incubated with anti-human ICAM-1 antibody (Cell Signaling Technology, Danvers, Mass.) in 1% BSA PBS overnight at 4° C. The cells were washed with PBS-Tween and incubated with the secondary antibody (HRP-conjugated anti-rabbit IgG, Dako Ltd., Glostrup, Denmark). The ICAM-1 signal was detected by adding substrate and reading the absorbance at 450 nm against a reference wavelength of 655 nm using a spectrophotometer. The cells were then washed with PBS-Tween and total cell numbers in each well were determined by reading absorbance at 595 nm after Crystal Violet staining and elution by 1% SDS solution. The measured OD 450-655 readings were corrected for cell number by dividing with the OD595 reading in each well. The inhibition of ICAM-1 expression was calculated at each concentration of test compound by comparison with vehicle control. The 50% inhibitory concentration (IC$_{50}$) was determined from the resultant concentration-response curve.

The invention claimed is:

1. A compound of formula (I):

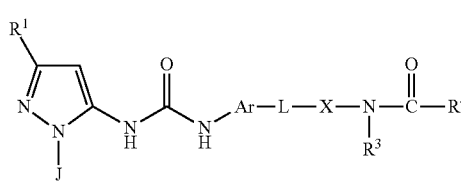

(I)

wherein:

J represents

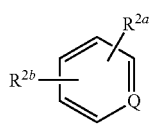

Ar is a naphthylene;
Q is CH;
$R^1$ is a saturated branched or unbranched $C_{1-10}$ alkylene chain;
$R^{2a}$ is saturated branched or unbranched $C_{1-8}$ alkylene chain;
$R^{2b}$ is H;
L is selected from the group consisting of —O, —OCH$_2$—, —OCH$_2$CH$_2$—, S and SO$_2$;

X is a pyridine ring;
R³ is H;
R⁴ is $C_{1-10}$ branched or unbranched, unsubstituted alkyl chain; or a pharmaceutically acceptable salt thereof, including all stereoisomers, tautomers and isotopic derivatives thereof.

2. A compound of formula (I) according to claim 1, wherein R¹ is methyl, ethyl, propyl, iso-propyl, butyl or tert-butyl.

3. A compound of formula (I) according to claim 1, wherein R¹ is tert-butyl.

4. A compound of formula (I) according to claim 1, wherein $R^{2a}$ is in the ortho, meta or para position.

5. A compound of formula (I) according to claim 1, wherein $R^{2a}$ is methyl, ethyl, n-propyl, iso-propyl, n-butyl or tert-butyl, in particular methyl.

6. A compound of formula (I) according to claim 1, wherein $R^{2a}$ is methyl.

7. A compound of formula (I) according to claim 1, wherein L is O.

8. A compound of formula (I) according to claim 1, wherein L represents —OCH₂— or —OCH₂CH₂—.

9. A pharmaceutical composition comprising a compound according to claim 1, in combination with one or more pharmaceutically acceptable diluents or carriers.

10. The compound according to claim 1, wherein the compound is selected from the group consisting of N-(4-(2-(4-(3-(3-tert-Butyl-1-p-tolyl-1H-pyrazol-5-yl)ureido)4yridine4ne-1-yloxy)ethyl)4yridine-2-yl)acetamide;

N-(4-(((4-(3-(3-(tert-Butyl)-1-(p-tolyl)-1H-pyrazol-5-yl)ureido)4yridine4ne-1-yl) oxy)methyl)4yridine-2-yl)acetamide; and N-(4-((4-(3-(3-(tert-Butyl)-1-(p-tolyl)-1H-pyrazol-5-yl)ureido)4yridine4ne-1-yl) oxy)4yridine-2-yl)acetamide.

11. The compound according to claim 1, wherein
$R^{2a}$ is methyl;
L is O; and
R⁴ is methyl.

12. The compound according to claim 1, wherein
$R^{2a}$ is methyl;
L is —OCH₂—; and
R⁴ is methyl.

13. The compound according to claim 1, wherein
$R^{2a}$ is methyl;
L is —OCH₂CH₂—; and
R⁴ is methyl.

* * * * *